(12) United States Patent
Bosworth et al.

(10) Patent No.: US 10,426,393 B2
(45) Date of Patent: Oct. 1, 2019

(54) SYSTEMS AND METHODS FOR MONITORING PILOT HEALTH

(71) Applicant: Aurora Flight Sciences Corporation, Manassas, VA (US)

(72) Inventors: William Robert Bosworth, Somerville, MA (US); Zarrin Khiang-Huey Chua, Boston, MA (US); Jessica Edmonds Duda, Wayland, MA (US); Eugene H. Nahm, Allston, MA (US)

(73) Assignee: Aurora Flight Sciences Corporation, Manassas, VA (US)

( * ) Notice: Subject to any disclaimer, the term of this patent is extended or adjusted under 35 U.S.C. 154(b) by 0 days.

(21) Appl. No.: 16/032,679

(22) Filed: Jul. 11, 2018

(65) Prior Publication Data

US 2019/0090800 A1   Mar. 28, 2019

Related U.S. Application Data

(60) Provisional application No. 62/562,152, filed on Sep. 22, 2017.

(51) Int. Cl.
*A61B 5/18* (2006.01)
*A61B 5/00* (2006.01)
(Continued)

(52) U.S. Cl.
CPC .............. *A61B 5/18* (2013.01); *A61B 5/0015* (2013.01); *B64D 45/00* (2013.01); *A61B 5/01* (2013.01);
(Continued)

(58) Field of Classification Search
USPC ....................................... 340/573.1, 971–980
See application file for complete search history.

(56) References Cited

U.S. PATENT DOCUMENTS

| 5,920,276 A | 7/1999 | Frederick |
| 6,927,694 B1 * | 8/2005 | Smith ................. B60K 28/066 |
| | | 340/573.1 |

(Continued)

FOREIGN PATENT DOCUMENTS

| DE | 102014211852 A1 | 12/2015 |
| EP | 2916309 A1 | 9/2015 |

(Continued)

OTHER PUBLICATIONS

Akerstedt, T. & Gillberg, M.; Subjective and Objective Sleepiness in the Active Individual., Intern. J. Neurosci., 1990, 62: pp. 29-37.

(Continued)

*Primary Examiner* — Joseph H Feild
*Assistant Examiner* — Sharmin Akhter
(74) *Attorney, Agent, or Firm* — Michael Stanley Tomsa; McAndrews, Held & Malloy, Ltd.; Eugene H. Nahm

(57) ABSTRACT

Pilot health monitoring systems, methods, and apparatuses are provided. A pilot health monitoring system is configured to collect information regarding the pilot's physiological and/or physical characteristics, and information regarding a state of the aircraft; analyze the information; determine a health condition of the pilot and/or a state of the aircraft; and/or provide warnings and/or commands as a function of the information.

25 Claims, 19 Drawing Sheets

(51) Int. Cl.
| | |
|---|---|
| B64D 45/00 | (2006.01) |
| G16H 50/30 | (2018.01) |
| A61B 5/1455 | (2006.01) |
| A61B 5/01 | (2006.01) |

(52) U.S. Cl.
CPC ....... *A61B 5/14551* (2013.01); *A61B 2503/22* (2013.01); *B64D 2045/004* (2013.01); *B64D 2045/0035* (2013.01); *B64D 2045/0045* (2013.01); *B64D 2045/0055* (2013.01); *G16H 50/30* (2018.01)

(56) References Cited

U.S. PATENT DOCUMENTS

| | | | |
|---|---|---|---|
| 6,948,681 | B2 | 9/2005 | Stupakis |
| 8,260,736 | B1 | 9/2012 | Lear et al. |
| 8,265,818 | B2 | 9/2012 | Allport |
| 8,384,534 | B2 | 2/2013 | James et al. |
| 8,437,890 | B2 | 5/2013 | Anderson et al. |
| 9,296,401 | B1 | 3/2016 | Palmer et al. |
| 9,557,742 | B2 | 1/2017 | Paduano et al. |
| 9,919,712 | B1 * | 3/2018 | Doyen .................. B60W 40/08 |
| 9,958,875 | B2 | 5/2018 | Paduano et al. |
| 2001/0026316 | A1 | 10/2001 | Senatore |
| 2003/0093187 | A1 | 5/2003 | Walker |
| 2008/0125920 | A1 | 5/2008 | Miles et al. |
| 2009/0050750 | A1 | 2/2009 | Garrec et al. |
| 2009/0055038 | A1 | 2/2009 | Garrec et al. |
| 2010/0152933 | A1 | 6/2010 | Smoot et al. |
| 2011/0017863 | A1 | 1/2011 | Goossen et al. |
| 2011/0068224 | A1 | 3/2011 | Kang et al. |
| 2011/0139928 | A1 | 6/2011 | Morris et al. |
| 2011/0174931 | A1 | 7/2011 | Berland |
| 2011/0245996 | A1 | 10/2011 | Orsulak et al. |
| 2012/0065881 | A1 | 3/2012 | McIver et al. |
| 2012/0075119 | A1 | 3/2012 | Dorneich et al. |
| 2012/0091259 | A1 | 4/2012 | Morris et al. |
| 2012/0233447 | A1 | 9/2012 | Fitzgerald |
| 2012/0319869 | A1 * | 12/2012 | Dorfmann ................. A61B 5/18 340/945 |
| 2013/0008998 | A1 | 1/2013 | Morris et al. |
| 2013/0054054 | A1 | 2/2013 | Tollenaere et al. |
| 2013/0116856 | A1 | 5/2013 | Schadeck |
| 2013/0200207 | A1 | 8/2013 | Pongratz et al. |
| 2014/0124621 | A1 | 5/2014 | Godzdanker et al. |
| 2014/0180914 | A1 | 6/2014 | Abhyanker |
| 2014/0240132 | A1 | 8/2014 | Bychkov |
| 2014/0276090 | A1 | 9/2014 | Breed |
| 2014/0316616 | A1 | 10/2014 | Kugelmass |
| 2015/0012186 | A1 | 1/2015 | Horseman |
| 2015/0323932 | A1 | 11/2015 | Paduano et al. |
| 2016/0090097 | A1 | 3/2016 | Grube et al. |
| 2017/0029103 | A1 | 2/2017 | Chang et al. |
| 2017/0073071 | A1 | 3/2017 | Salzmann et al. |
| 2017/0090480 | A1 | 3/2017 | Ho et al. |
| 2017/0277185 | A1 | 9/2017 | Duda et al. |

FOREIGN PATENT DOCUMENTS

| | | |
|---|---|---|
| EP | 2933788 A2 | 10/2015 |
| GB | 2543503 A | 4/2017 |
| WO | 2015/200224 A2 | 12/2015 |
| WO | 2016/118672 A2 | 7/2016 |
| WO | 2016/164416 A1 | 10/2016 |

OTHER PUBLICATIONS

M. Whalley et al., "The NASA/Army Autonomous Rotorcraft Project," American Helicopter Society 59th Annual Forum, May 6-8, 2003.

Bergasa, L. M., Nuevo, J., Sotelo, M. A., Barea, R., & Lopez, M. E.; Real-Time system for Monitoring Driver Vigilance, IEEE Transactions on Intelligent Transportation Systems, vol. 77, No. 1, Mar. 2006, 63-77.

Oman, C. M., & Liu, A. M. (2007). Locomotive In-Cab Alerter Technology Assessment, Excerpted from: Development of Alternative Locomotive In-Cab Alerter Technology: Final Technical Report DOT Volpe PR#79-3389, DTS-79, Volpe National Transportation Systems Center, Cambridge, MA, Nov. 30, 2006.

Ji, Q., Lan, P., & Looney, C.; A Probabilistic Framework for Modeling and Real-Time Monitoring Human Fatigue. IEEE Transactions on Systems, Man, and Cybernetics—Part A: Systems and Humans, 2006, 36(5), 862-875.

Riener, A., & Ferscha, A.; Reconfiguration of Vibro-tactile Feedback based on Drivers' Sitting Attitude. 2009 Second International Conferences on Advances in Computer-Human Interactions (pp. 234-242). IEEE.

Heikenfeld, Jason, "Sweat Sensors Will Change How Wearables Track Your Health," IEEE Spectrum, Oct. 22, 2014.

Gould, Joe, "Precision Airdrop System Land at CENTCOM on Time," Defense News, Dec. 19, 2014.

Peláez, G.A., Garcia, F., Escalera, A., & Armingol, J. M.; Driver Monitoring Based on Low-Cost 3-D Sensors, IEEE Transactions on Intelligent Transportation Systems, 2014, 15(4), pp. 11687-11708.

Abd-Elfattah, H. M., Abdelazeim, F. H., & Elshennawy, S.; Physical and cognitive consequences of fatigue: A review. Journal of Advanced Research (2015) 6, 351-358.

Solomon, C., & Wang, Z.; Driver Attention and Behavior Detection with Kinect. J. Image Graph, 3(2), Dec. 2015, 84-89.

Pilot incapacitation occurrences 2010-2014, Australian Transport Safety Bureau, Report No. AR-2015-096, published Feb. 18, 2016.

Kiesielowski, E. et al., "Technical Report No. LWL-CR-09M71, Rough Terrain Ground Handling System for Helicopters," Final Report, U.S. Army Land Warfare Laboratory, Apr. 1974.

Whalley, M. et al., "Field-Testing of a Helicopter UAV Obstacle Field Navigation and Landing System," American Helicopter Society 65th Annual Forum Proceedings, Ft. Worth, Texas, May 2009.

S. Lange et al., "A Vision Based Onboard Approach for Landing and Position Control of an Autonomous Multirotor UAV in GPS-Denied Environments", Jul. 2009.

K-MAX Unmanned Aircraft System brochure, Copyright 2010 Lockheed Martin Corporation.

Chamberlain, L. et al., "Self-Aware Helicopters: Full-Scale Automated Landing and Obstacle Avoidance in Unmapped Environments," American Helicopter Society 67th Annual Forum Proceedings, Virginia Beach, Virginia, May 2011.

J. Paduano et al., "TALOS: An Unmanned Cargo Delivery System for Rotorcraft Landing to Unprepared Sites," American Helicopter Society 71st Annual Forum Proceedings, Virginia Beach, Virginia, May 2011.

"Autonomous Aerial Cargo/Utility System (AACUS): Concept of Operations (CONOPs)," The Office of Naval Research, Dec. 22, 2011.

Dollar, Aaron "Aerial Grasping and Manipulation," the GRAB Lab, Yale University, 2012.

M. Verbandt et al., "Robust marker-tracking system for vision-based autonomous landing of VTOL UAVs," IMAV 2014.

J. Paduano et al., "TALOS: An unmanned cargo delivery system for rotorcraft landing to unprepared sites," Jan. 2015.

Morton, Kye et al., "Development of a Robust Framework for an Outdoor Mobile Manipulatio UAV," 978-1-4673-7676-1/16$31.00 © 2016 IEEE.

IPR Petition PTAB-IPR2018-01704—dated Sep. 11, 2018.

R. Brockers et al., "Autonomous landing and ingress of micro-air-vehicles in urban environments based on monocular vision", Apr. 25, 2011.

Office of Naval Research, Broad Agency Announcement No. 12-004.

Extended European search report for Application No. 18192059.6, dated Feb. 4, 2019.

Extended European search report for Application No. 18194074.3, dated Feb. 11, 2019.

Extended European search report for Application No. 18195738.2, dated Feb. 13, 2019.

(56) References Cited

OTHER PUBLICATIONS

Extended European search report for Application No. 18195747.3, dated Feb. 25, 2019.

* cited by examiner

| Vital sensor Indication | Behavioral Indication | Incapacitation/Alert Level Determination |
|---|---|---|
| Green | Green | Green |
| Green | Yellow | Green |
| Green | Red | Yellow |
| Yellow | Green | Yellow |
| Yellow | Yellow | Yellow |
| Yellow | Red | Red |
| Red | Green | Yellow |
| Red | Yellow | Red |
| Red | Red | Red |

Figure 11

SYSTEMS AND METHODS FOR MONITORING PILOT HEALTH

CROSS-REFERENCE

The present application claims the benefit under 35 U.S.C. § 119(e) of U.S. Provisional Patent Application Ser. No. 62/562,152, filed Sep. 22, 2017, and titled "Systems and Methods for Monitoring Pilot Health," the contents of which are hereby incorporated by reference.

TECHNICAL FIELD

The present disclosure relates to the field of flight control systems, methods, and apparatuses; even more particularly, to a system, method, and apparatus for performing an emergency descent and landing operation via an aircrew automation system functioning as a robotic co-pilot.

BACKGROUND

Modern aircraft, such as a typical commercial jet, are capable of cruising altitudes ranging from 30 to 40 thousand feet. Some aircraft, such as some non-commercial jets, can reach cruising altitudes above 65 thousand feet. Operating in such high altitudes exposes the people on board (e.g., a pilot, crewmember, passengers) to conditions that may have a negative effect on the body. A person's health can therefore be adversely affected by extended exposures to conditions associated with high altitude, especially above the person's tolerance level. This and other situations can put those travelling in aircraft at risk.

Recent experience with automation in cockpits has shown that prior approaches of adding additional functionality to flight decks increases complexity, causes overreliance on automation, and may not necessarily reduce workload, especially during critical situations. An additional challenge is that avionics manufacturers have instituted strict requirements-based design and change orders for any desired improvements, in order to provide high reliability and verifiability. Thus, conversion of legacy aircraft is generally cost prohibitive and requires a large capital investment in requirements, verification, and testing.

Aurora Flight Sciences Corporation of Manassas, Va. has previously developed a right-seat pilot assistant capable of operating a Diamond DA42 Twin Star during takeoff, cruise, and landing. The right-seat pilot assistant, called Centaur, can be installed into, and removed from, the DA42 without affecting the original type certificate, thus maintaining the aircraft's original certification. Centaur includes mechanical actuation of the primary flight controls and its own avionics suite, and may be used with a pilot in a supervisory role or as a fully unmanned aircraft. For example, Centaur may be flown by an operator in the back seat of the airplane, directing the flight plan on a laptop. While Centaur offers many features, it suffers from certain drawbacks. In particular, (1) the Centaur hardware is not portable to other aircraft, nor is the software plug-and-play extensible to other capabilities; (2) parts of the Centaur system are invasive and require cutting into existing avionics wiring in a manner very specific to the aircraft (i.e., the DA42); (3) Centaur does not allow the onboard pilot to be the operator and to perform tasks such as directing the flight plan; and (4) Centaur does not acquire knowledge about the aircraft it is operating.

Thus, a need exists for an open architecture system that enables quick introduction of new capabilities, increases safety, grows functionality, and reduces pilot workload—without large expense or recertification. There is also a need to provide a pilot with continuous aircraft state monitoring and information augmentation, which can effectively serve as an automated flight engineer. In addition, a need exists for a system and method to perform an emergency descent and landing through operation of existing auto landing capability in an aircraft, for example, in the case of pilot incapacitation. Indeed, the tragic occurrence of unexpected pilot incapacitation requires that the healthy pilot (when two pilots are available) perform a solo descent and landing. An aircrew automation system, such as is disclosed herein, addresses these needs and enables new capabilities to be rapidly introduced to mitigate burden while being portable across airframes (e.g., via temporary installations). As will be discussed, the aircrew automation system can provide significant benefit to a variety of end-users. An example application includes the operation of aircraft where fatigue and boredom can cause a reduction in crew attentiveness, in which case the aircrew automation system reduces risk in a flight operation by alerting the pilot and, in certain instances, assuming control of the aircraft. Other example applications exist where the potential for human error currently limits extensive use of aircraft (e.g., low-altitude operations), synchronized operations, unmanned flights, unmanned formations with manned flight lead, and improved debrief capabilities due to comprehensive data logging.

SUMMARY OF THE INVENTION

The present disclosure is directed to pilot health monitoring systems, methods, and apparatuses. Even more particularly, a system, method, and apparatus is configured to collect information regarding the pilot's physiological and/or physical characteristics, and information regarding a state of the aircraft; analyze the information; determine a health condition of the pilot and/or a state of the aircraft; and/or provide warnings and/or commands as a function of the information.

An exemplary system for monitoring a pilot's health condition during flight may include a pilot monitoring system having a plurality of sensors, an aircraft state monitoring system, and/or a core platform. The pilot monitoring system may be in communication with a data storage, a communication system, and/or a pilot computing device.

Additionally, the present disclosure provides flight control systems, methods, and apparatuses configured to, inter alia, automatically perform an emergency descent and landing in the event of pilot incapacitation.

According to a first aspect, a pilot monitoring system for use in an aircraft comprises: a plurality of sensors configured to monitor one or more health parameters of a pilot; an aircraft state monitoring system configured to determine flight situation data of the aircraft; an analysis system to determine, via one or more processors, an incapacitation level of the pilot as a function of the one or more health parameters; and a human machine interface operatively coupled with the one or more processors to provide an interface between the pilot and the pilot monitoring system, the human machine interface configured to present a warning to the pilot as a function of the determined incapacitation level.

In certain aspects, the pilot monitoring system further comprises an actuation system operatively coupled with the one or more processors to adjust or actuate one or more flight controls of the aircraft as a function of the determined incapacitation level.

In certain aspects, the pilot monitoring system is configured to monitor one or more health parameters for each of a plurality of pilots, wherein the human machine interface is configured to display the one or more health parameters for each of the plurality of pilots.

In certain aspects, the one or more health parameters include both a physiological state and a behavioral state of the pilot.

In certain aspects, the actuation system is configured to perform an emergency descent procedure as a function of the determined incapacitation level, wherein, during the emergency descent procedure, the pilot monitoring system is configured to navigate the aircraft, via the actuation system, to a predetermined airspeed and a predetermined altitude.

In certain aspects, during the emergency descent procedure, the actuation system is configured to automatically: (1) adjust or actuate the one or more flight controls to descend the aircraft from a cruising altitude to the predetermined altitude; (2) adjust or actuate the one or more flight controls to slow the aircraft from a cruising airspeed to the predetermined airspeed; (3) alert an air traffic control facility of an emergency situation; and (4) set and hold the aircraft in a holding pattern at or near its current position.

In certain aspects, the actuation system is configured to perform an auto-landing procedure, wherein, during the auto-landing procedure, the pilot monitoring system is configured to navigate the aircraft, via the actuation system, from the predetermined altitude to a touchdown location.

In certain aspects, during the auto-landing procedure, the actuation system is configured to automatically: (1) adjust or actuate the one or more flight controls; (2) adjust an airspeed of the aircraft; (3) adjust or actuate an autobrake; (4) determine a glideslope for the aircraft to the touchdown location; (5) adjust or actuate landing gear; and (6) adjust or actuate one or more reverse thrusters.

In certain aspects, the actuation system is configured to control the secondary flight controls of the aircraft during the auto-landing procedure.

In certain aspects, the actuation system includes an XY-plotter defining a Y-axis and an X-axis, a tool to engage at least one of the aircraft's secondary flight controls, and a control system to move the tool along the Y-axis and the X-axis.

In certain aspects, the plurality of sensors includes one or more optical sensors to monitor the pilot visually, wherein the pilot monitoring system determines a behavioral state of the pilot based at least in part on the visual monitoring gathered by the one or more optical sensors.

In certain aspects, the pilot monitoring system is configured to determine whether the pilot is incapacitated based at least in part on the behavioral state for the pilot.

In certain aspects, the analysis system is configured to compute a point of gaze for the pilot using one or more eye-tracking techniques, wherein the pilot monitoring system is configured to determine whether the pilot is incapacitated based at least in part on the point of gaze for the pilot.

In certain aspects, the pilot monitoring system is configured to gather the one or more health parameters for the pilot using one or more wearable vital sensors associated with the pilot.

In certain aspects, the human machine interface is configured to display a plurality of tasks via a touch screen display in a form of a task list during the auto-landing procedure, wherein each of the plurality of tasks is marked as either completed or not completed during the auto-landing procedure based at least in part on an input provided via the touch screen display or an operation of the aircrew automation system.

In certain aspects, the plurality of sensors is configured to monitor one or more cockpit instruments of the aircraft visually to generate the flight situation data.

According to a second aspect, a method for monitoring a pilot in an aircraft using an automation system comprises the steps of: monitoring, via a plurality of sensors, one or more health parameters for the pilot; determining, via an aircraft state monitoring system, flight situation data of the aircraft; determine, via an analysis system, an incapacitation level of the pilot, wherein incapacitation level is determined as a function of the one or more health parameters; and presenting a warning to the pilot, via a human machine interface, as a function of the determined incapacitation level, wherein the human machine interface is configured to provide an interface between the pilot and the automation system.

In certain aspects, the method further comprises the step of adjusting or actuating, via an actuation system, one or more flight controls of the aircraft as a function of the determined incapacitation level.

In certain aspects, the method further comprises the step of performing an emergency descent procedure as a function of the determined incapacitation level, wherein, during the emergency descent procedure, the automation system is configured to navigate the aircraft, via the actuation system, to a predetermined airspeed and a predetermined altitude.

In certain aspects, the method further comprises the step of performing an auto-landing procedure, wherein, during the auto-landing procedure, the automation system is configured to navigate the aircraft, via the actuation system, from the predetermined altitude to a touchdown location.

In certain aspects, during the auto-landing procedure, the actuation system is configured to automatically: (1) adjust or actuate the one or more flight controls; (2) adjust an airspeed of the aircraft; (3) adjust or actuate an autobrake; (4) determine a glideslope for the aircraft to the touchdown location; (5) adjust or actuate landing gear; and (6) adjust or actuate one or more reverse thrusters.

In certain aspects, the automation system is configured to gather the one or more health parameters for the pilot using one or more wearable vital sensors associated with the pilot.

In certain aspects, the plurality of sensors includes one or more optical sensors to monitor the pilot visually, wherein the automation system is configured to determine a behavioral state of the pilot as a function of information gathered by the one or more optical sensors.

In certain aspects, the method further comprises the step of computing a point of gaze for the pilot through one or more eye-tracking techniques, wherein the pilot monitoring system is configured to determine whether the pilot is incapacitated based at least in part on the point of gaze for the pilot.

In certain aspects, the plurality of sensors is configured to monitor one or more cockpit instruments of the aircraft visually to generate the flight situation data.

DESCRIPTION OF THE DRAWINGS

These and other advantages of the present disclosure may be readily understood with the reference to the following specifications and attached drawings wherein:

FIG. 1b illustrates an example flow of information data between the subsystems of FIG. 1a.

FIG. 11 illustrates an example classification structure.

DETAILED DESCRIPTION

Figure 1A:
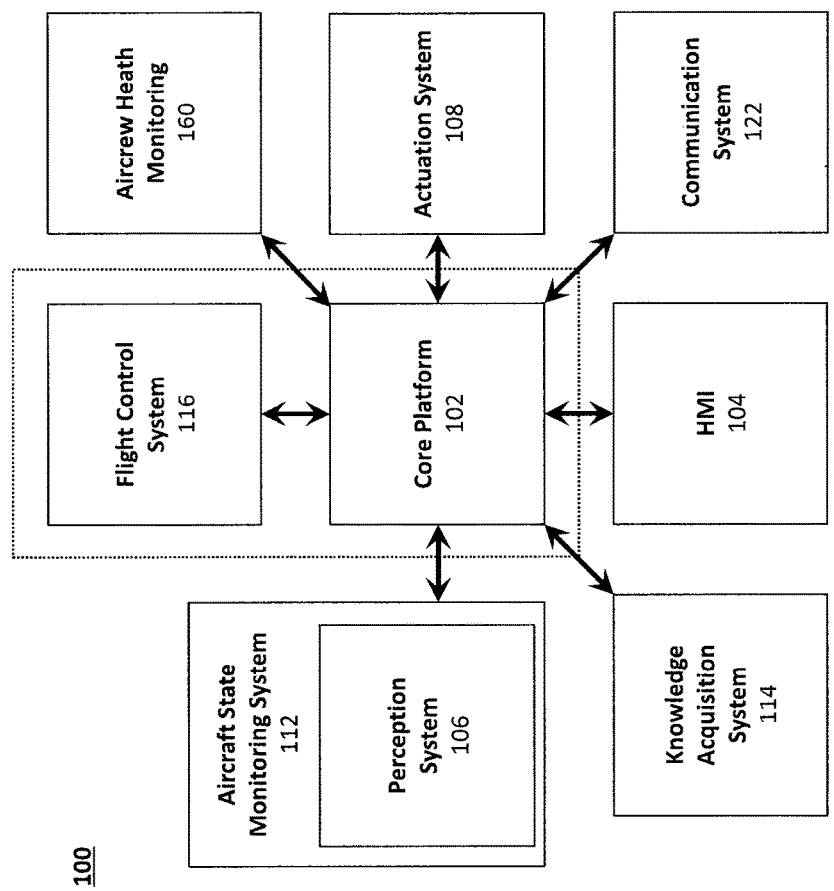
FIG. 1a illustrates a block diagram of an example aircrew automation system.

Preferred embodiments of the present disclosure may be described hereinbelow with reference to the accompanying drawings. In the following description, well-known functions or constructions are not described in detail because they may obscure the disclosure in unnecessary detail. For this disclosure, the following terms and definitions shall apply.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first set of one or more lines of code and may comprise a second "circuit" when executing a second set of one or more lines of code.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations.

As used herein, the words "about" and "approximately," when used to modify or describe a value (or range of values), mean reasonably close to that value or range of values. Thus, the embodiments described herein are not limited to only the recited values and ranges of values, but rather should include reasonably workable deviations. As utilized herein, circuitry or a device is "operable" to perform a function whenever the circuitry or device comprises the necessary hardware and code (if any is necessary) to perform the function, regardless of whether performance of the function is disabled, or not enabled (e.g., by a user-configurable setting, factory trim, etc.).

As used herein, the terms "aerial vehicle" and "aircraft" refer to a machine capable of flight, including, but not limited to, both traditional runway and vertical takeoff and landing ("VTOL") aircraft. VTOL aircraft may include fixed-wing aircraft (e.g., Harrier jets), rotorcraft (e.g., helicopters), and/or tilt-rotor/tilt-wing aircraft.

As used herein, the terms "communicate" and "communicating" refer to (1) transmitting, or otherwise conveying, data from a source to a destination, and/or (2) delivering data to a communications medium, system, channel, network, device, wire, cable, fiber, circuit, and/or link to be conveyed to a destination. The term "database" as used herein means an organized body of related data, regardless of the manner in which the data or the organized body thereof is represented. For example, the organized body of related data may be in the form of one or more of a table, a map, a grid, a packet, a datagram, a frame, a file, an e-mail, a message, a document, a report, a list, or data presented in any other form.

The present disclosure provides a system and method for monitoring a pilot's health condition during flight. The pilot's health condition may be monitored by physiological and/or physical measurements of the pilot's vital signs and/or analysis of behavioral traits during flight. Once the pilot's health condition is determined, a response can be initiated, such as a warning and/or an emergency procedure to maintain proper and/or safe operation of the aircraft.

Disorientation, fatigue, incapacitation, etc., of a pilot can occur for a variety of reasons, including development of an acute medical condition (such as hypoxia), changes in environmental conditions during flight, and/or the effects of a pre-existing medical condition. According to the Australian Transport Safety Bureau (ATSB), an average of 23 pilot incapacitation occurrences were reported between the years of 2010 and 2014. During that time, there were 113 occurrences of flight crew incapacitation reported to the ATSB. Other causes of flight crew incapacitation include gastrointestinal illness (i.e. food poisoning), laser strikes, to name but a few.

Operators have taken steps to prepare for such emergency situations that may occur during flight. For example, each pilot is provided a different meal to prevent the pilots from becoming ill from a single cause, such as food poisoning. Crewmembers are trained to attend to certain medical conditions of a pilot as well. Nonetheless, these methods and protocols assume there will be either two or more pilots or multiple crewmembers on board during flight.

While a multi-pilot crew may be able to handle an emergency, an aircraft operating with a single pilot, with or without additional crewmembers, would face catastrophic consequences in the event of an incapacitating medical situation.

Therefore, a need exists for a system configured to monitor and/or identify the health of a pilot during flight. Based on the system's analysis, a determination can be made as to whether to take further action, such as generate a warning for the pilot, carry out an emergency medical procedure, take control of the airplane controls, etc. For example, if the system determines the pilot is incapacitated or otherwise unable to control the aircraft, the system can control the aircraft to enter into an emergency mode, initiate an automated landing procedure, etc. In an example, the system can control the aircraft to fly at a lower altitude and loiter until the pilot's health condition returns to normal and/or until a remote or automated pilot can take control of the aircraft.

Also disclosed herein is a system configured to, inter alia, function as a pilot's assistant (or co-pilot) or flight engineer. Such an aircrew automation system may be configured to operate an aircraft from takeoff to landing, automatically executing the necessary flight and flight plan activities, checklists, and procedures at the correct phases of flight, while detecting contingencies or emergencies and responding to them. At the same time, the pilot (e.g., a human pilot or operator) may be continuously informed through an intuitive human-machine interface operatively coupled with the aircrew automation system. That is, the aircrew automation system may provide real-time information and/or feedback to the pilot. For example, the aircrew automation system may indicate a state of the aircraft relative to the procedure being accomplished. The aircrew automation system may be configured to take back control of the aircraft through robotic actuators, if desired.

In doing so, the pilot is enabled to perform tasks best suited for humans, such as high-level decision-making and flight plan planning. Tasks best suited for automation, however, may be handled by the aircrew automation system, including, for example, the manipulation of controls, executing checklists, monitoring aircraft engine and performance data, and monitoring aircrew health and attentiveness. Additionally, the aircrew automation system may have the capability to access external information that is either currently unavailable to pilots or that which only comes with experience, such as common system failures for a particular aircraft or how air traffic control commonly routes traffic at a particular airport. The aircrew automation system may be configured to operate as an assistant or as the primary pilot (i.e., captain), thereby, if so configured, entirely obviating the need for a human operator. Alternatively, the aircrew automation system may serve to provide a pilot with continuous aircraft state monitoring and information augmentation, without actually taking control of the aircraft. For example, the aircrew automation system may serve as a "second set of eyes" for the pilot, monitoring checklists, instrumentation, engine state, airspace, flight regime, etc. The aircrew automation system may further perform, or supervise, an automatic descent and land procedure in an aircraft—such may be the case in an emergency situation.

Unlike existing robotic autopilots and pilot assist systems, which are invasive to the aircraft, require considerable installation expertise, and are aircraft-specific, an aircrew automation system in accordance with an aspect of the present disclosure employs a system architecture and knowledge acquisition system that enables rapid non-invasive installation, which facilitates widespread use and enables the aircrew automation system to be quickly adapted for use in a variety of aircraft. Further, the aircrew automation system's data collection and perception systems are not limited to GPS, accelerations, orientation, and heading, as is the case with existing robotic autopilots. Indeed, the aircrew automation system exceeds the capability of existing data collection and perception systems to better capture aircraft performance by employing both standalone sensors, instrument image data capture (e.g., temperature, altitude, radar, flap angles, etc.), and measuring, detecting, or otherwise receiving pilot inputs or parameters. Further, the aircrew automation system's core platform and design of the primary and secondary flight control actuation systems enables portability across a variety of aircraft. Thus, unlike existing robotic autopilots or pilot assist systems, the aircrew automation system may be temporarily installed and readily transferred from aircraft to aircraft, without invasive modification to the aircraft. The aircrew automation system, through its modular design, further reduces the likelihood of designing a single point solution that becomes obsolete as aircraft evolve.

The aircrew automation system's combination of subsystems provides a pilot with high-fidelity knowledge of the aircraft's physical state, and notifies that pilot of any deviations in expected state based on, for example, predictive models. This state awareness may be translated directly into useful information for the pilot, such as alerts to developing emergency conditions, fuel state computation, notification of icing conditions, etc. For example, the aircrew automation system may also serve as an automated flight engineer, thereby advising the pilot by monitoring checklists, instrumentation, engine state, airspace, flight regime, etc. The aircrew automation system's combination of subsystems may also provide a pilot, or other aircrew member, with high-fidelity knowledge of the pilot's physical state, and notifies that pilot of any health alerts based on, for example, actual measurement and/or predictive models.

This ride-along aircrew automation system, which may be non-invasively installed in preexisting aircraft, perceives the state of the aircraft and pilot visually and via other sensors, derives the aircraft state vector and other aircraft or pilot information, and communicates any deviations from expected aircraft state to the pilot or an airport control tower. While the aircrew automation system may be non-invasively installed (e.g., via a perception system), it may alternatively be invasive. For example, the aircrew automation system may electronically couple with the cockpit instrument panel (e.g., via the reverse side of the instrument panel) via, for example, the aircraft state monitoring system. Alternatively, the aircrew automation system may be integral and permanently installed during fabrication of the aircraft. In conjunction with an actuation system, the aircrew automation system may further take control of the aircraft and autonomously navigate the aircraft by controlling its primary and/or secondary controls.

System Level Architecture.

Figure 1B:
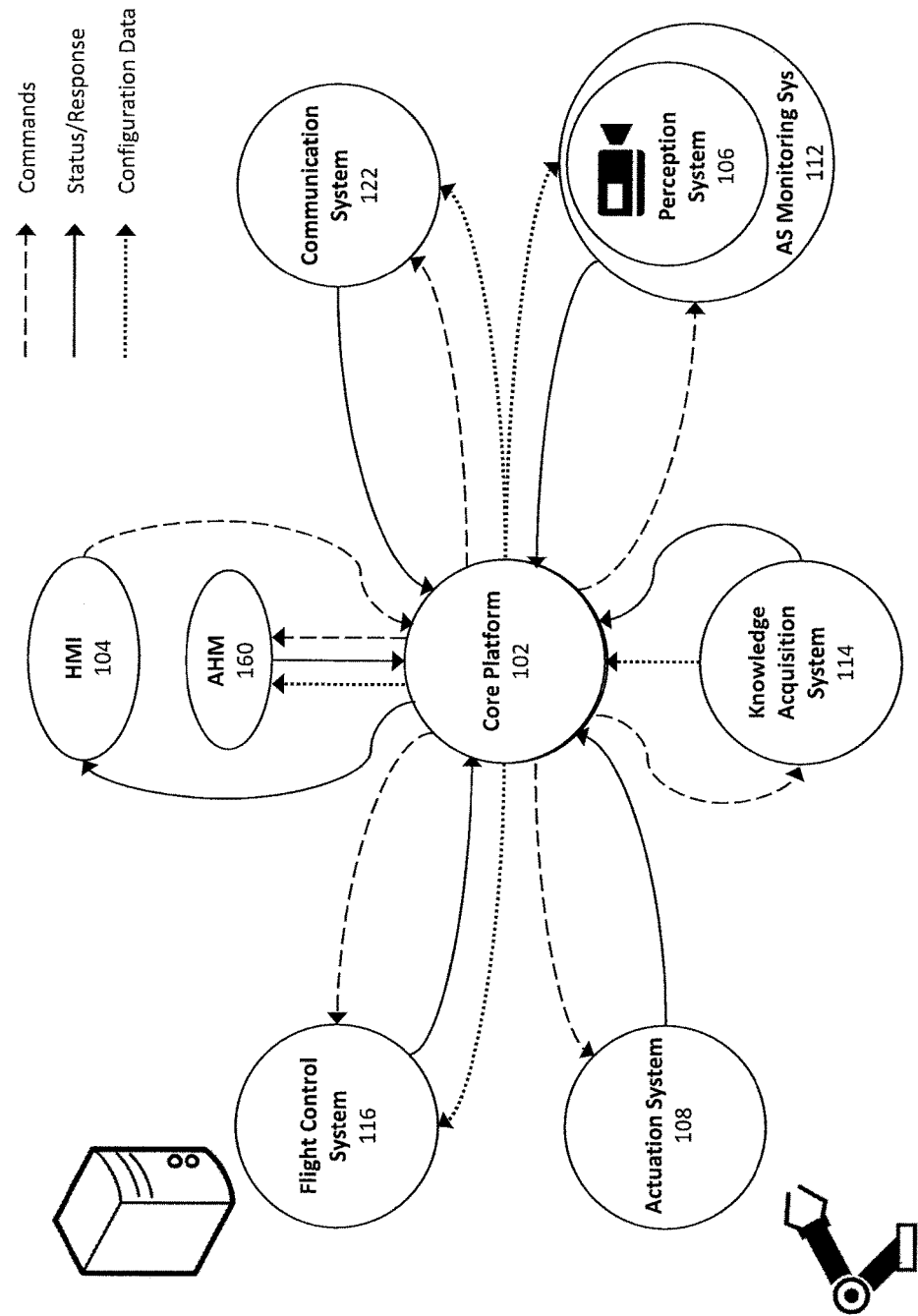
Figure 1C:
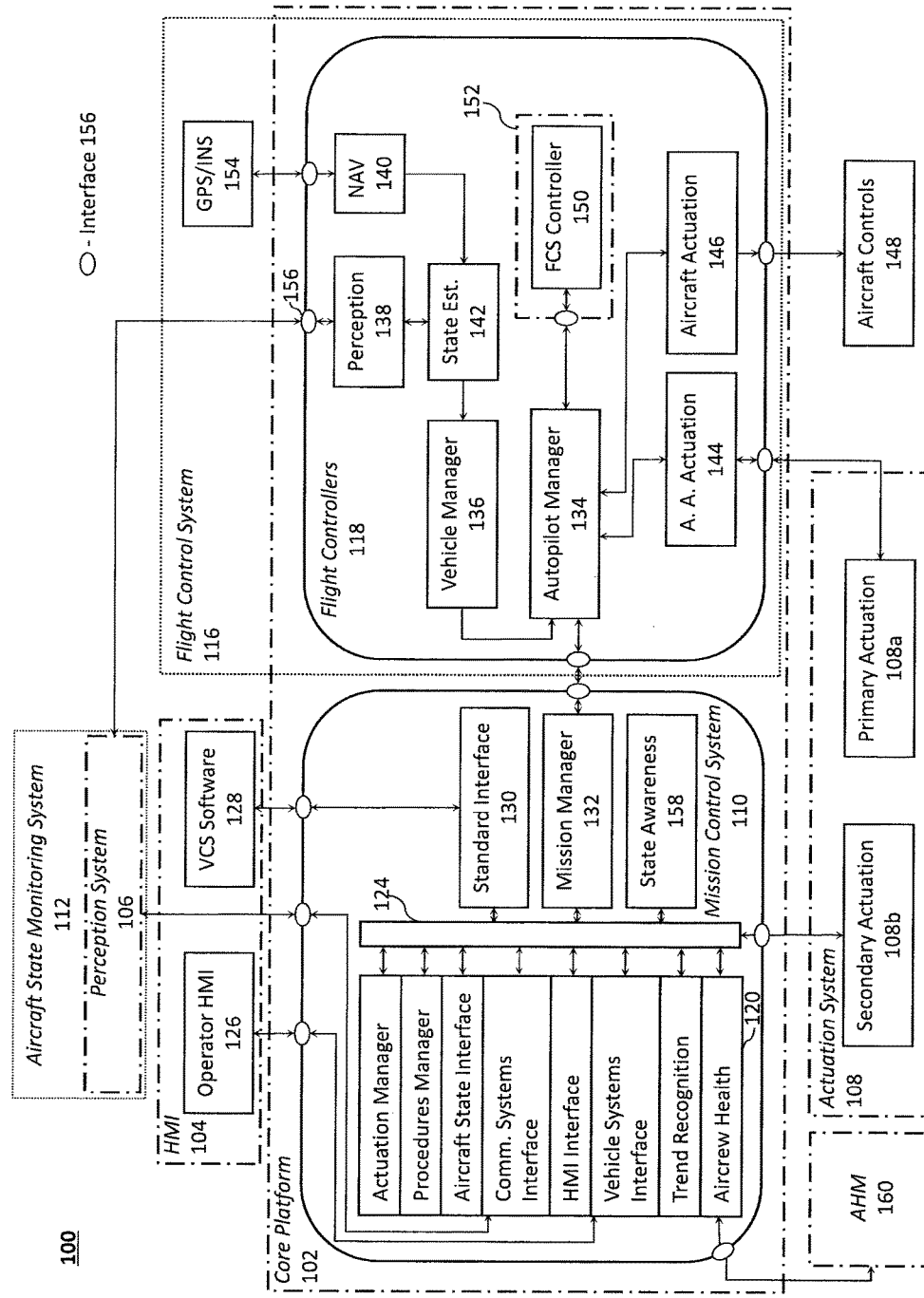
FIG. 1c illustrates a block diagram of an example core platform.

To share the duties and workload related to the execution of flight activities, the aircrew automation system 100 should be capable of executing the actions a pilot would perform routinely over the duration of a flight through landing, regardless of the aircraft make, model, or type. An example system architecture for an aircrew automation system 100 in accordance with one aspect is shown in FIGS. 1a through 1c. As illustrated in FIG. 1a, the core platform 102 may operate as a central subsystem that connects the other subsystems via one or more interfaces. The subsystems may communicate with one another through software and/or hardware interfaces 156 using wired and/or wireless communication protocols and hardware. FIG. 1b illustrates an example flow of information (e.g., data) between the various subsystems.

The aircrew automation system 100 may comprise a core platform 102 operatively coupled with a plurality of subsystems, such as those listed below. Each of the plurality of subsystems of the aircrew automation system 100 may be modular, such that the entire aircrew automation system 100 can be disconnected and substantially ported to another aircraft rapidly. For example, the various subsystems may be removably and communicatively coupled to one another via the core platform 102 using one or more software and/or hardware interfaces 156. In certain aspects, however, the aircrew automation system 100 may alternatively be integral with the aircraft's system, thereby directly employing all sensors and indicators in the airplane. For example, the aircrew automation system 100, or components thereof, may be integrated into the aircraft during its design and manufacturing.

The plurality of subsystems may include, for example, a perception system 106, an actuation system 108, a human machine interface ("HMI") system 104, a flight control system 116, and an aircrew health monitoring ("ABM") system 160, each of which may be operatively coupled with the core platform 102. In certain aspects, the need for a perception system 106 may be mitigated or obviated via use of another aircraft state monitoring system. For example, the aircrew automation system 100 may couple (e.g., communicatively or electronically) with the instrument panel, or be otherwise integrated with the aircraft or its systems. As can be expected, however, such integration would be invasive to the aircraft as it would require a degree of modification to the aircraft or its wiring. The aircrew automation system 100 and/or core platform 102 may also comprise, or be operatively coupled to, a knowledge acquisition system 114 and a communication system 122. The modular configuration further enables the operator to remove/disable unnecessary systems or modules or to add/install additional systems or modules. For example, when the aircrew automation system 100 is configured to provide only information to the pilot via the HMI system 104 (i.e., without the ability to control the aircraft), the actuation system 108 may be removed or disabled to reduce weight, cost, and/or power consumption. Accordingly, depending on the configuration, the aircrew automation system 100 may be configured with fewer or additional modules, components, or systems without departing from the spirit and scope of the disclosure.

In operation, the flight control system 116 derives the pilot and aircraft state based on information data from another subsystem (e.g., perception system 106 or aircrew health monitoring system 160) and directs another subsystem (e.g., the actuation system 108) to operate (e.g., dynamically—in real-time or near real-time) in a manner to maintain aircraft stability. For example, the flight control system 116 may receive vehicle mode commands and configuration data from the core platform 102, while sending to the core platform 102 status and command information generated by the flight control system 116. Indeed, the core platform may be configured to communicate one or more commands to the flight control system 116 of the aircraft based at least in part on the flight situation data, which may be obtained from the aircraft state monitoring system 112, the perception system 106, or a combination thereof.

The flight control system 116 may include, or communicate with, existing flight control devices or systems, such as those used in fixed wing aircraft and rotary wing aircraft. The communication system 122 enables the aircrew automation system 100 to communicate with other devices (including remote or distant devices) via, for example, a network. The communication system 122 may receive communication commands and configuration data from the core platform 102, while sending to the core platform 102 status and response information from the communication system 122.

Core Platform 102.

Figure 2:
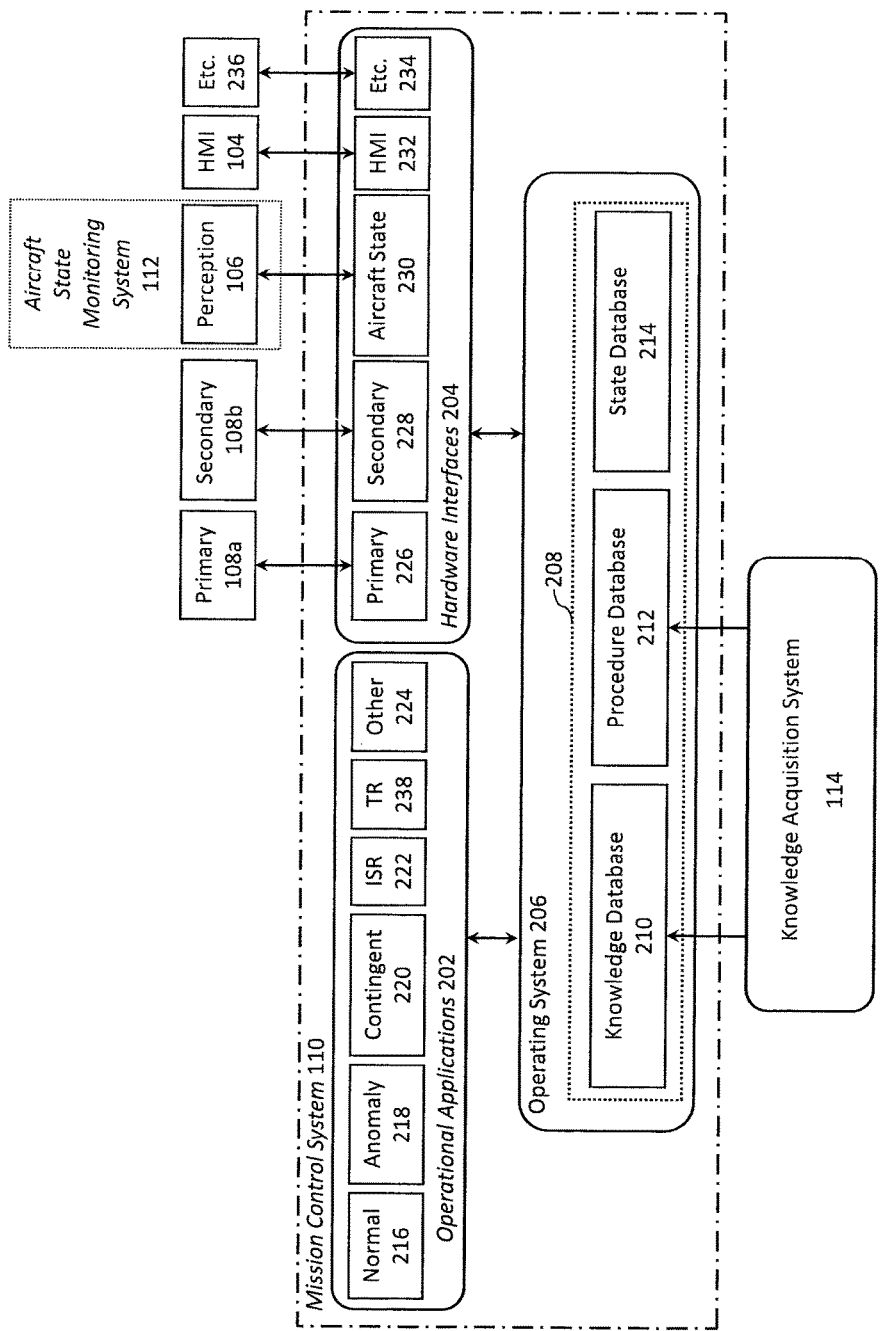
FIG. 2 illustrates a diagram of an example core platform architecture.

FIG. 2 illustrates an architecture diagram of an example core platform 102. To enable a vehicle-agnostic aircrew automation system 100, a core platform 102 may provide, or otherwise serve as, middleware that can be made specific to a particular aircraft or configuration through an initial transition and setup phase. In other words, the mission control system 110 may provide an operating system 206 that provides services to a set of operational applications 202 and output signals to one or more of a set of hardware interfaces 204 or HMI system 104, while collecting and logging the data necessary to enable those applications.

The core platform 102 serves as the primary autonomous agent and decision-maker, which synthesizes inputs from the perception system 106 and HMI system 104 with its acquired knowledge base to determine the overall system state. The core platform 102 may employ a processor to process inputs from the various sensor suites or subsystems and aggregate the resultant information into an understanding of current aircraft state. The resultant information may be compared against an aircraft specific file that encompasses the aircrew automation system's 100 understanding of pilot intent, system health, and understanding of appropriate aircraft procedures as they relate to the aircrew automation system's 100 state estimation. The resultant state knowledge and associated recommendations can be passed to a human pilot via the HMI system 104 or, in certain aspects, to the flight control system 116 and/or actuation system 108 to enable autonomous operation. The aircrew automation system 100 may further generate a log of a given flight for later analysis, which may be used to facilitate pilot training that can provide detailed training and operations flight debriefs. The logs may be used in connection with, for example, flight operational quality assurance analysis, maintenance analysis, etc.

As illustrated, the core platform 102 may comprise a mission control system 110 and flight controllers 118, each of which are configured to communicate with one another and the other subsystems via one or more software and/or hardware interfaces 156, which may be a combination of hardware (e.g., permanent or removable connectors) and software. The core platform 102 can host various software processes that track the aircraft and procedure states, as well as any modules for trend analytics (predictive warnings) and machine learning routines. In certain aspects, the aircrew automation system 100 and/or core platform 102 may employ a computer bus and specification (e.g., as an interface) that facilitates discovery of a hardware component of a subsystem within the aircrew automation system 100 without the need for physical device configuration or user intervention in resolving resource conflicts. Such a configuration may be referred to as "plug-and-play." Thus, a user may readily add or remove system or subsystems (e.g., as modules) to the aircrew automation system 100 via the core platform 102 without requiring substantive modification or integration efforts.

The core platform 102 outputs may be used to provide messages to the HMI system 104. The messages may indicate, for example, checklist progress, contingencies to initiate, warnings to raise, aircrew (e.g., pilot) health status, etc. The core platform 102 may also contain a flight data recorder, for instance to provide performance review capability and to provide robustness against in-flight reset. The hardware and various computers may also be ruggedized and share a housing with other devices, such as the perception computer. For example, the hardware and various computers may be ruggedized using improved wiring/connectors to pervert shorts and/or power or signal loss, thermal management, stronger mechanical structures, redundant components, and the like, which make the hardware and software tolerant to environmental conditions of the aircraft (e.g., vibration, temperature, pressure, etc.). As discussed below, the core platform 102 may be operatively coupled with a global positioning system ("GPS")/inertial navigation system ("INS") system 154 and power management system (e.g., 28 VDC power). The core platform 102 may also contain a flight data recorder, for instance to provide performance review capability and to provide robustness against in-flight reset.

The mission control system 110 generally comprises a mission manager 132, a standard interface 130 (e.g., a STANAG interface), a state awareness manager 158, and other operational components 120 (e.g., hardware and software controllers and/or interfaces), each of which are communicatively coupled to one another via one or more data buses 124. Other operational components 120 may include, for example, an actuation manager operational component, a procedures manager operational component, an aircraft state operational component, an HMI operational component, a vehicle systems operational component, a trend recognition operational component, and an aircrew health operational component. The open architecture of the core platform 102 enables the incorporation of additional data received from systems via the data bus 124. In certain aspects, the mission control system 110 may be coupled with one or more cockpit instruments of the aircraft via the vehicle systems interface to collect flight situation data. In other aspects, the mission control system 110 may collect flight situation data through an aircraft state interface via the aircraft state monitoring system 112, which may collect or generate flight situation data via a direct connection to the aircraft and/or the perception system 106.

As illustrated, the mission control system 110 may be operationally coupled with the secondary actuation system 108*b* (e.g., when autonomous operation is desired), the perception system 106, and the HMI system 104, including the human-machine interface 126 (e.g., software and/or hardware that conveys inputs from and displays information to the pilot), and ground station 128. The mission control system 110 may communicate with the flight controllers 118 via the mission manager 132.

The flight controllers 118 may include, for example, an autopilot manager 134 and a vehicle manager 136. The vehicle manager 136 may be generally responsible for navigation and determining the location and state of the aircraft. The vehicle manager 136 may be coupled with a state estimation module 142, which determines the estimated state of the aircraft using information received from the perception system 106 via a perception module 138 and from the GPS/INS system 154 via a navigation module 140.

The autopilot manager 134 may be generally responsible for controlling the aircraft's flight based on, for example, information received from the vehicle manager 136 and the mission control system 110. The autopilot manager 134 controls, inter alia, the flight control system 152, which may be new or preexisting (and comprises a flight controller 150), as well as the aircrew automation actuation module 144 and the aircraft actuation module 146. The aircrew automation actuation module 144 may control the primary actuation system 108*a*, while the aircraft actuation module 146 may control the aircraft controls 148 (e.g., various flight surfaces and actuators).

In certain aspects, the flight controller's 118 components may overlap with certain components of the flight control system 116. For example, in certain aspects (e.g., where redundancy is not desired and non-invasive integration is possible), the core platform 102 may exploit certain existing aircraft software and/or hardware, thereby obviating the need for additional hardware, such as certain flight controller 118 components and/or a GPS/INS system 154.

Open Architecture.

The core platform 102 serves as the central subsystem, or interface, of the aircrew automation system 100, connecting and controlling the remaining subsystems (e.g., as individual applications) in an open architecture. The remaining subsystems include, for instance, the flight control system 116 (including any flight plan capabilities), the HMI system 104, the actuation systems 108 (e.g., the primary and secondary actuation systems to provide autonomous operation where desired), the perception system 106, knowledge acquisition system 114, and other subsystems 236, such as the aircrew health monitoring system 160. Thus, control of the other aircrew automation system 100 hardware may be provided via separate applications specific to a particular piece of hardware, which enables rapid integration of new systems or other external flight plan support technology.

The core platform's 102 architecture enables rapid portability and extensibility when transitioning to a new aircraft or incorporating a new flight plan feature/capability. Thus, an application may be used to enable the aircrew automation system 100 to acquire information specific, or otherwise needed, for that aircraft or to provide the new capability. For example, transition and setup can be handled by individual applications that operate within the core platform 102 or other subsystems, representing aircraft-specific functionalities as well as a growing library of capabilities of aircrew automation system 100, which can be exchanged depending on flight plan, aircraft or crew requirements. In certain aspects, the transition process may be supported by software applications external to the aircrew automation system 100 (such as a procedure editor).

Aircraft Data Structure 208.

The operating system 206 operates as the middleware, interconnecting the operational applications 202, hardware interfaces 204, and other subsystems, such as the knowledge acquisition system 114. The operating system 206 may employ an aircraft data structure 208, which may include a knowledge database 210, a procedure database 212, and a state database 214.

The aircraft data structure 208 facilitates a vehicle-agnostic aircrew automation system 100 by enabling the core platform 102 to develop a complete understanding of an aircraft's systems, their configuration, and the procedures necessary to maintain safe operation, and all other knowledge and expertise a certified pilot of that aircraft would be expected to have. The core platform 102 may also develop a complete understanding of the aircrew health. The aircraft data structure 208 may be populated by the knowledge acquisition system 114 (discussed below), which contains necessary information about the aircraft currently being operated (e.g., flight control model, operational procedures, aircraft systems, etc.), data received from internal state sensors, and other subsystems or sensors.

The aircraft data structure 208 can be populated and adjusted to a specific aircraft during a knowledge acquisition phase (e.g., during initial setup) such that it contains all the information necessary to operate the aircraft. For example, when transitioning to a new aircraft, the knowledge acquisition system 114 may perform predefined activities in order to determine the layout (e.g., of the controllers/read outs, such as the cockpit instruments), performance parameters, and other characteristics of the aircraft. The predefined activities may include, for example: (1) generation of an aircraft system model, which informs aircrew automation system 100 about which systems are onboard and how they are configured, actuation limits, etc.; (2) procedure codification, which informs aircrew automation system 100 how to operate aircraft in normal and non-normal situations, further including the codification of checklists; (3) an aerodynamic model, which informs the aircrew automation system 100 how to fly the aircraft and what performance to expect for which aircraft configurations; and (4) information about mission operations.

The core platform 102 can combine this information with data from a set of internal state sensors, which also improve redundancy and system robustness, thereby allowing the aircrew automation system 100 to generate a highly accurate estimate of the aircraft state and system statuses, and to identify deviation from expected behavior. During flight operations, the data structure is dynamically updated with real-time data gathered by, inter alia, the aircrew automation system's 100, perception system 106, the HMI system 104, as well as the aircrew automation systems 100 internal state sensing. Once the aircraft data structure 208 for a given aircraft is populated, the aircraft data structure 208 can then be retained in an aircraft library and used for all other aircraft of the same make and model for which aircrew automation system 100 is available. The aircraft data structure 208 may be further refined as additional data is generated and/or collected by the aircrew automation system 100.

Operational Applications 202.

The core platform 102 may provide the aircrew automation system 100 with a plurality of operational applications 202. Examples of such operational applications 202 might include, without limitation, normal flight operation application 216, an anomaly detection application 218, a contingency operation application 220, an intelligence, surveillance, and reconnaissance ("ISR") application 222 (e.g., ISR orbits), a trend recognition application 238, or other flight plan-specific activity applications 224, such as an aerial refueling application 316.

The normal flight operation application 216 enables aircrew automation system 100 to fly a predetermined flight plan from takeoff to landing, assuming no contingencies. The normal flight operation application 216 is specific to the continuous execution of normal flight activity, as needed by a particular flight phase. The predetermined flight plan may be modified in flight due to unexpected disturbances such as weather, air traffic control commands, air traffic, etc.

The anomaly detection application 218 employs machine learning techniques to monitor aircraft state, cluster, and classify sensor inputs in order to detect the presence of non-normal situations, and to identify whether a contingency has occurred. The anomaly detection application 218 is configured to compare the sensed states against a set of thresholds defined in the operational documentation for the specific aircraft (e.g., never exceed a predetermined airspeed, engine temperature, etc.). The anomaly detection application 218 may also compare the sensed states against additional information available to aircrew automation system 100 and generate alerts or other messages in response to meeting predetermined or dynamically determined thresholds (e.g., warning thresholds, etc.).

In case of a contingency condition, a contingency operation application 220 executes the necessary predetermined checklists, procedures, and actions specified by the contingency operation application 220 in order to maintain safe operation of the aircraft or safely divert the flight. Notably, if a departure from expected performance is observed, the pilot can be alerted to a non-normal condition, thereby mitigating or avoiding potential mistakes. If an aircraft is susceptible to a particular operational error (e.g., pilot induced oscillations), the aircrew automation system 100 can identify and mitigate such events. If an anomaly is detected, the contingency operation application 220 informs and interacts with the pilot via the HMI system 104 and ultimately executes the necessary procedure(s) to respond to the anomaly. Finally, the ISR application 222 and other flight plan-specific activity applications 224 may provide instructions, algorithms, or information to carry out operations relevant to a mission.

The trend recognition application 238 provides trend analysis developed using machine learning based on, for example, the knowledge acquisition system 114. In certain aspects, the trend recognition application 238 may supply data, or otherwise trigger, the anomaly detection application 218. For example, if the trend recognition application 238 detects an undesirable trend, the trend may be flagged as an anomaly and reported to the anomaly detection application 218.

Hardware Interfaces 204.

The various information pertaining to the operational applications 202 are communicated between the primary actuation system 108a, secondary actuation system 108b, perception system 106, aircraft state monitoring system 112, HMI system 104, and other subsystems 236 via, for example, the primary actuation interface 226, secondary actuation interface 228, aircraft state interface 230, HMI interface 232, and other interface 234.

Human/Machine Interface (HMI) System 104.

The HMI system 104 provides a control and communication interface for the pilot (e.g., a human pilot, whether on-board or remote). The HMI system 104 is configurable to operate as a flight plan manager that enables the pilot to direct the aircrew automation system 100. The HMI system 104 can combine elements of glass cockpits, unmanned aerial vehicle ("UAV") ground stations, and electronic flight bags (EFB) to enable effective, efficient and latency-tolerant communication between the pilot and aircrew automation system 100. Generally speaking, an EFB is an electronic information management device that allows flight crews to perform a variety of functions that were traditionally accomplished by using paper references. The HMI system 104 may include a human-machine interface 126, which may be based on a touch screen graphical user interface ("GUI") and/or speech-recognition systems. The human-machine interface 126 may employ, for example, a tablet computer, a laptop computer, a smart phone, head mounted display, or combination thereof. The human-machine interface 126 can be secured near the pilot (e.g., on the yoke—as checklists often are, or on a knee-strap) depending on pilot preferences. The human-machine interface 126 may be removable coupled to the cockpit or, in certain aspect, employ an integrated display within the cockpit (e.g., an existing display).

Figure 3A:
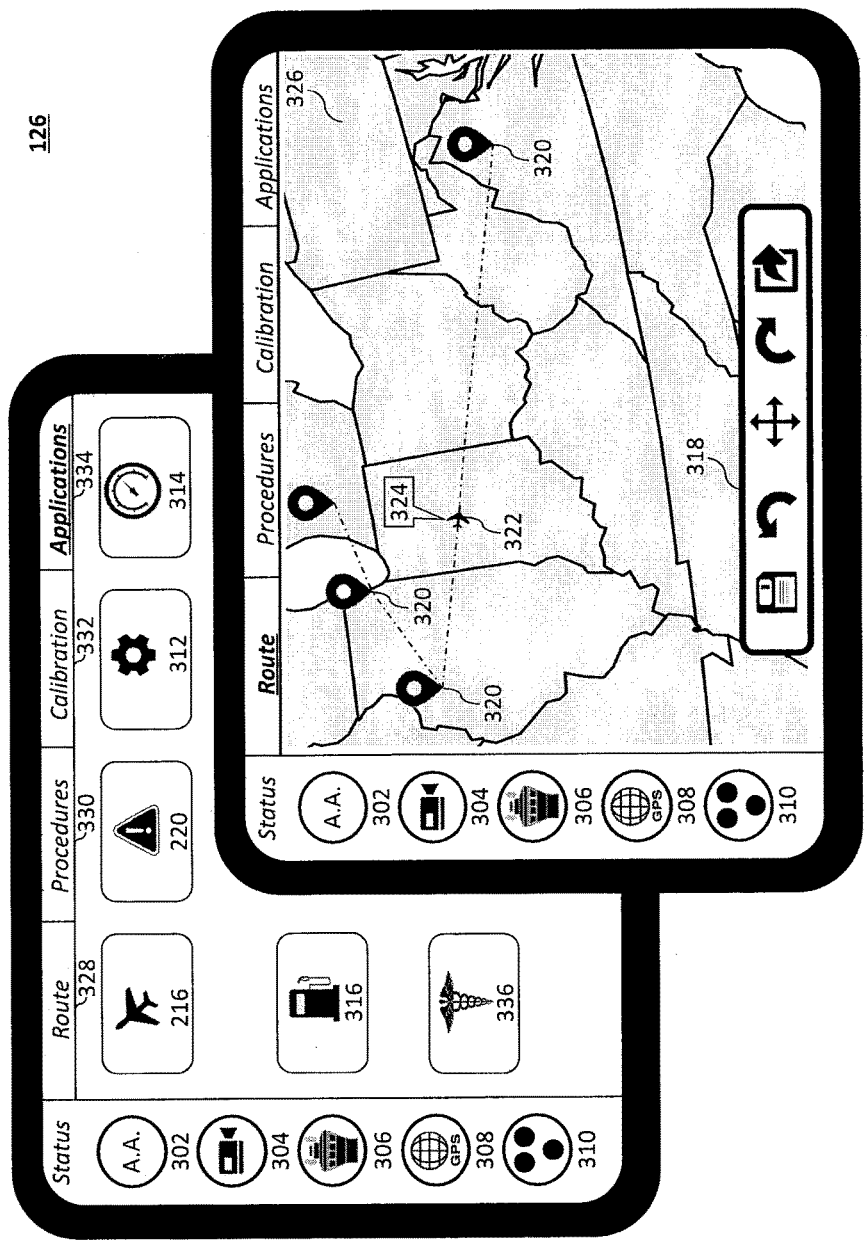
FIG. 3a illustrates a first example human-machine interface illustrating a route application.

FIG. 3a illustrates an example human-machine interface 126 having a single-screen touch interface and speech-recognition system. The HMI system 104 serves as a primary channel of communication between the pilot and the aircrew automation system 100, enabling the pilot to command tasks to and receive feedback or instructions from the aircrew automation system 100, to change the allocation of tasks between pilot and aircrew automation system 100, and to select which operational applications 202 are currently enabled for the aircrew automation system 100.

As illustrated in FIG. 1b, for example, the HMI system 104 may receive status information from a subsystem via the core platform 102, while sending to the core platform 102 mode commands generated by the HMI system 104 or input by the pilot. The pilot may be remote (e.g., on the ground or in another aircraft) or on-board (i.e., in the aircraft). Thus, in certain aspects, the HMI system 104 may be remotely facilitated over a network via communication system 122.

Human-Machine Interface 126.

Figure 3B:
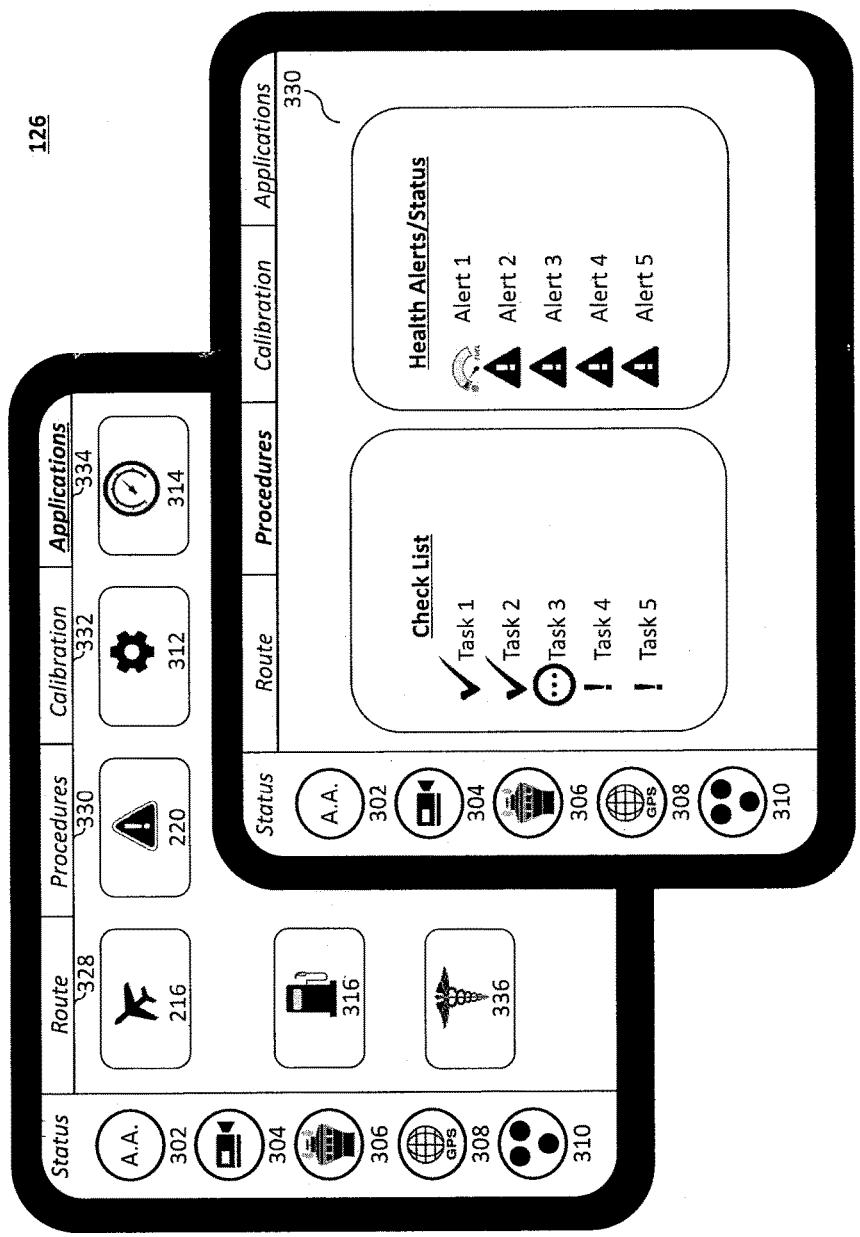
FIG. 3b illustrates a second example human-machine interface illustrating a procedural checklist and aircraft health alert screen.
Figure 3C:
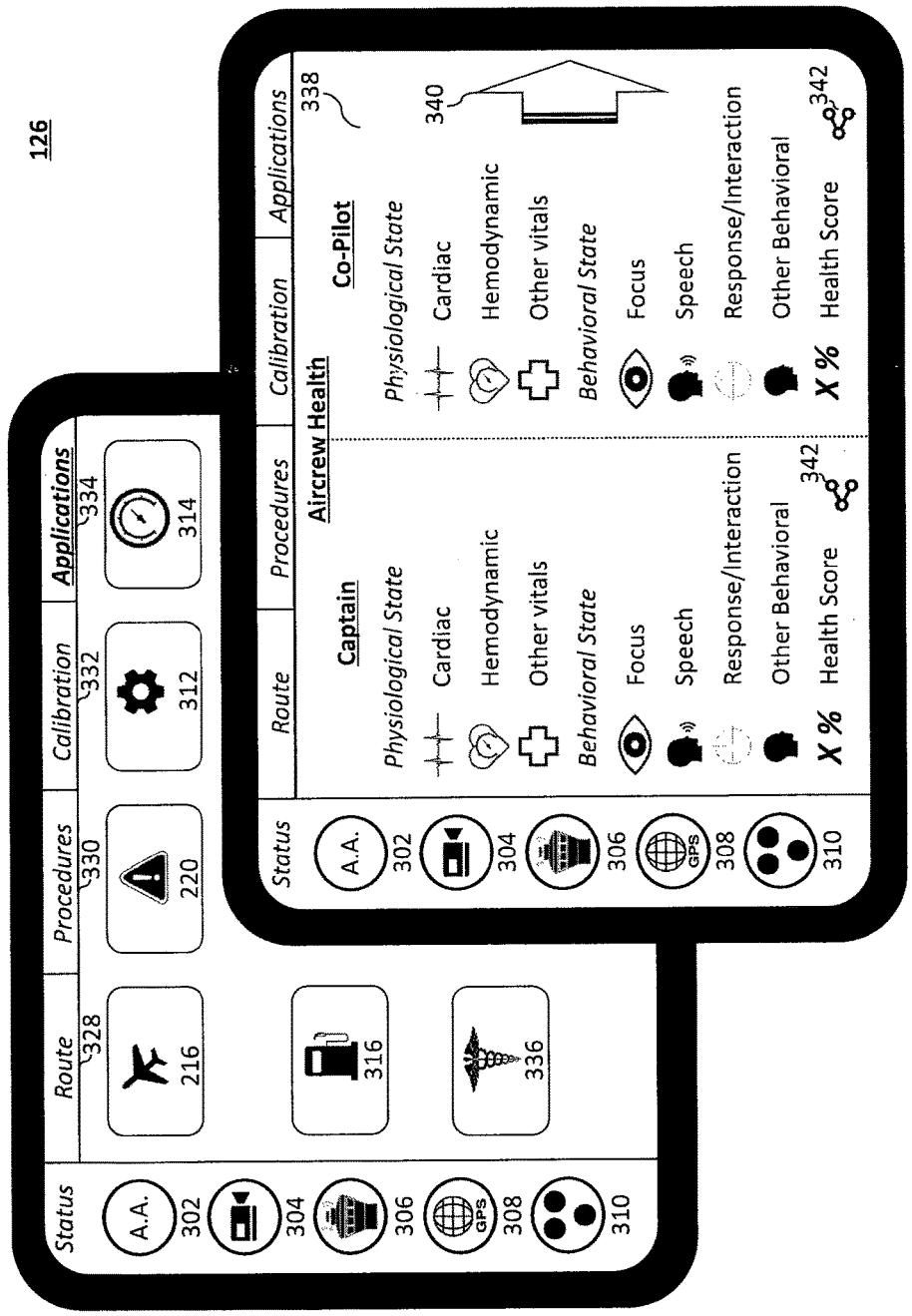
FIG. 3c illustrates a third example human-machine interface illustrating a pilot health alert screen.

As illustrated in FIGS. 3a and 3b, the human-machine interface 126 may employ a tablet based GUI and a speech-recognition interface that enables vocal communications. An objective of the human-machine interface 126 is to enable the pilot to interact with the core platform 102's knowledge base in manner akin to the way a pilot interacts with a human flight engineer or copilot.

The human-machine interface 126 can display, via a display device (e.g., a liquid crystal display (LCD)), the current state of aircrew automation system 100 (its current settings and responsibilities) as well as which operational applications 202 are currently installed, which operational applications are running and, if they are active, which actions the operational applications 202 are taking. The human-machine interface 126's GUI display may also be night-vision goggles compatible such that it is visible regardless of the pilot's eyewear. The speech-recognition system may be used to replicate the same types of verbal communications used by human aircrew when running through checklists and communicating on the flight deck. In certain aspects, the speech recognition may be limited to the same standards of codified communications used by pilot teams to minimize the chances of the system failing to recognize commands or changing into inappropriate modes of operations. The speech-recognition system may be configured to learn/recognize the speech of a given pilot through a voice training protocol. For example, the pilot may speak a predetermined script such that the speech-recognition system can become trained with the pilot's dialect.

The human-machine interface 126 may communicate the status and/or details of various operations, including the entire aircrew automation system 100 via the aircrew automation status application 302, the perception system 106 via the perception status application 304, the autopilot via the autopilot status application 306 (where applicable), the GPS/INS system 154 via the GPS status application 308, the aircrew health monitoring system 160 via the aircrew health application 336, and any other application or system status information 310. The display of the human-machine interface 126 may be customized by the pilot. For example, the pilot may wish to add, reorganize, or remove certain of the display icons and/or operational applications 202, which may be accomplished through a select and drag maneuver or through the aircrew automation settings application 312. The human-machine interface 126 may further inform the pilot regarding the aircraft's operating status and to provide the pilot with instructions or advice.

As illustrated, the human-machine interface 126 may provide a tool bar with various selectable tabs, such as a route tab 328, a procedures tab 330, a calibration tab 332, and an applications tab 334. When the pilot selects the applications tab 334, for example, the human-machine interface 126 may display the various operational applications 202 installed on the aircrew automation system 100 (e.g., the core platform 102), including, for example, a normal flight operation application 216, a contingency operation application 220, an aircrew automation settings application 312, gauge application 314, and aerial refueling application 316.

Selecting the aircrew automation settings application 312 enables the pilot to change, reallocate, or otherwise edit the settings of the aircrew automation system 100 and/or to install operational applications 202. Selecting the gauge application 314 may cause the human-machine interface 126 to display the various operational conditions of the aircraft, including, for example, position, direction, airspeed, altitude, pitch, yaw, etc. The various operational conditions of the aircraft, which may be gathered from the perception system 106 or another sensor, may be displayed as alpha-numeric characters or as graphical dials (e.g., in accordance with the pilot's preference settings). Finally, selecting the aerial refueling application 316 icon may cause the aircrew automation system 100 to perform a predetermined protocol for facilitating or coordinating a mid-air refueling operation. For example, upon selecting the aerial refueling application 316, the aircrew automation system may coordinate with another aircraft to facilitate refueling and perform the necessary checklists for doing the same (e.g., ensuring aircraft position, airspeed, fuel hatch opening, etc.). Additional mission applications may be included that enable performance of mission operations by the aircrew automation system.

When the pilot selects the route tab 328, the human-machine interface 126 may display an area map 326 with an icon 322 representing the current location of the aircraft along a flight path relative to its various waypoints 320. Selecting (e.g., tapping, clicking, etc.) the icon 322 may cause a dialog window 324 to display that provides the various operational conditions of the aircraft. The area map 326 may be saved, exported, rotated, or panned using a map control window 318. The area map 326 may be saved or exported (e.g., via communication system 122) as a static image or a data set (or database). When the pilot selects the calibration tab 332, the human-machine interface 126 may display the calibration of the aircraft, whereby the pilot may be further enabled to revise the same.

The HMI system 104 may provide an intuitive display and interface that includes checklist verification and health alerts from the core platform 102 and predictions of aircraft state (e.g., fuel consumption and predicted remaining range), as well as failure prognosis and deviation alerts (e.g., "Left Engine EGT Is 5 Degrees Above Normal And Rising"). Thus, when the pilot selects the procedures tab 330, as illustrated in FIG. 3b, the pilot may review and monitor checklist items, as well as review any health alerts. Indeed, a function of the HMI system 104 is to facilitate checklist monitoring and/or execution, marking items as complete when the when the perception system 106 perceives their completion and providing warnings to the pilot when items are not completed, as based on information previously imported from, for example, a Pilot's Operating Handbook (POH). The aircrew automation system 100 also monitors system health, comparing the current system state to that expected based on the POH and other knowledge sources, and guides appropriate responses to contingencies. In certain aspects, either the pilot or the core platform 102 can acknowledge checklist actions as they are performed and the HMI system 104 automatically proceeds to the correct checklist as appropriate. The HMI system 104 may give visual and auditory alerts to direct the pilot's attention to unattended checklist items, instruments that are displaying out-of-normal range values, or predicted events as the aircraft proceeds through the flight plan, which can be entered as a series of waypoints (for instance). For example, as illustrated, a list of tasks may be provided alongside indicators that indicate whether the task has been completed, is being completed, or needs to be completed (e.g., a "check mark" icon to include complete, an "in progress" icon, and a "to be completed" icon). Similarly, a list of health hazards may be provide, along with one or corresponding icons to indicated one or more operational conditions that are out of range. For example, a low fuel indicator may be provided alongside a low fuel icon if fuel is low.

Aircrew Health Monitoring.

Selecting the aircrew health application 336 icon causes the aircrew automation system 100 to display an aircrew health overview display 338 with one or more physiological states and/or behavioral states of the aircrew member (e.g., the pilot, whether the primary pilot/captain, co-pilot, etc.) from the aircrew health monitoring system 160. The information on the aircrew health overview display 338 may be provided dynamically (e.g., in real-time or near real-time). Depending on the size of the display, a selectable arrow 340 (e.g., a GUI icon on the display) may be provided to enable the operator to page or scroll through the available aircrew members. A default setting, however, may display the most flight-important crew members, such as the captain and co-pilot.

The one or more physiological states may include cardiac parameters (e.g., ballistocardiograms, heart rhythm, heart rate in beats per minute (bpm), etc.), hemodynamic parameters (e.g., blood pressure and blood flow), and other vitals available from the aircrew health monitoring system 160, such as respiratory parameters, neurological parameters, body temperature, etc. The one or more behavioral states may include the aircrew member's focus, speech quality, responsiveness (e.g., based on timeliness of interaction with the HMI system 104) and other behavioral statuses, such as body posture, eye gaze, etc. In certain aspects, the aircrew health overview display 338 may display, for each monitored aircrew member, a health score (e.g., as a percentage).

The health score may be calculated based upon the one or more physiological states and/or behavioral states of the aircrew member to provide an indication of risk. For example, a 100% health score may indicate minimal risk of incapacitation (e.g., passing out, falling asleep, dying), while a score between 75 and 99% may indicate a slight risk of incapacitation, a score between 50 and 74% may indicate a moderate risk of incapacitation, and a score below 50% indicates a high risk of incapacitation. In lieu of percentages, other scales (e.g., alphabetical grading, such as A+, A, A−, B+, etc.), icons, or colors (e.g., green, yellow, red) may be used to indicate a health score. In certain aspects, the aircrew health application 336 may automatically launch to monitor (via the aircrew health monitoring system 160) and display (via the HMI system 104) health information for the members of the aircrew upon starting a flight or mission plan. During the flight, an operator may select the aircrew health application 336 icon to view the dynamic physiological states and/or behavioral states of the aircrew members. In certain aspects, the pilot may wish to communicate the physiological states and/or behavioral states of an aircrew member to the aircraft control tower by selecting a selectable share icon 342 (e.g., a GUI icon on the display), thereby keeping the aircraft control tower apprised of, for example, the pilots health and/or condition.

Task Allocation.

The HMI system 104 can enable the pilot to limit the activities executed by the aircrew automation system 100, if any. The HMI system 104 may define the allocation of tasks between the pilot and aircrew automation system 100, their responsibilities, and the communication of information between the two, thereby functioning as a collaborative teammate of the pilot. Thus, the aircrew automation system 100 may operate, depending on configuration, in a purely advisory role (i.e., without any control over the aircraft), a fully autonomous role (i.e., controlling the flight control without pilot intervention), or an advisory role with the ability to control flight controllers. The HMI system 104 may be further designed to enable a pilot to go through a transitional phase, where the pilot specifies the aspects of flight operation for which the aircrew automation system 100 is responsible. For example, the HMI system 104 may display a list of tasks where the pilot may select whether the aircrew automation system 100 or the pilot is responsible for a given task on the list. The list of tasks may be provided to the HMI system 104 from a procedure editor, which is described below. Once the aircraft data structure 208 has been populated and refined such that the pilot better trusts the aircrew automation system 100, the pilot may allow aircrew automation system 100 to perform additional actions, transitioning the pilot from a primary mode to a supervisory mode (i.e., a fully autonomous role). In this supervisory mode, pilot interactions may be at a high, goal-based level, with the HMI system 104 supporting those tasks as well as allowing the operator insight at other levels for troubleshooting. As noted above, in certain aspects, all tasks may be performed by the pilot, leaving the aircrew automation system 100 to serve an advisory role.

Mode Awareness.

A risk when employing any automation system is the potential for mode confusion on the part of the pilot (e.g., where the pilot neglects a task believing that the automation system will handle the task). The HMI system 104 avoids such mode confusion by first generating the correct function and the above-described task allocation between the aircrew automation system 100 and the pilot. Indeed, the HMI system 104 allows the pilot to directly command and configure aircrew automation system 100 via the human-machine interface 126 and displays the information necessary for the pilot to understand what actions the aircrew automation system 100 is taking to ensure mode awareness. In other words, mode awareness generally refers to a state where the mode of the system matches the operational mode expected by the operator. The human-machine interface 126 may display the information necessary to ensure that the pilot is always aware of the mode in which aircrew automation system 100 is operating. Additionally, the HMI system 104 serves as the human interface for individual mission applications (e.g., operational applications 202).

Aircraft State Monitoring System 112.

The aircraft state monitoring system 112 collects, determines, or otherwise perceives the real-time aircraft state. As noted above, the aircraft state monitoring system 112 may perceive the real-time aircraft state through, inter alia, a direct connection (e.g., integral with or otherwise hardwired to the aircraft) to the aircraft, or via perception system 106. When a perception system 106 is used, the aircraft state monitoring system 112 may include a dedicated controller (e.g., processor) or share the perception controller 402 of the perception system 106. The perception system 106, for example, may employ a combination of a vision system, an acoustic system, and identification algorithms to read or comprehend flight situation information displayed by cockpit instruments. Example cockpit instruments include, for example, an altimeter, an airspeed indicator, a vertical speed indicator, one or more compass systems (e.g., a magnetic compass), one or more gyroscopic systems (e.g., attitude indicator, heading indicator, turn indicator), one or more flight director systems, one or more navigational systems (e.g., very-high frequency omnidirectional range (VOR), non-directional radio beacon (NDB)), an instrument landing system (e.g., glide scope), etc. The perception system 106 may include a processor and one or more optical sensors (e.g., three or more lightweight machine vision cameras) trained on the instrument panel to maximizes pixel density, glare robustness, and redundancy. The one or more optical sensors may wiredly connect to the perception computer via, for example, Ethernet. The one or more optical sensors should be installed with a line of sight with the instrument panel, but so as to be not obstructive to the pilot.

The flight situation data perceived by the perception system 106 may be encoded and provided to the core platform 102 in real-time. The open architecture of the core platform 102 enables the incorporation of additional data received via a data bus 124 to augment the flight situation data generated by the perception system 106. As illustrated in FIG. 1b, for example, the aircraft state monitoring system 112 and/or the perception system 106 may receive commands and configuration data from the core platform 102, while sending to the core platform 102 status and flight situation information (e.g., flight situation data) gathered by the perception system 106 or otherwise collected by the aircraft state monitoring system 112.

Figure 4:
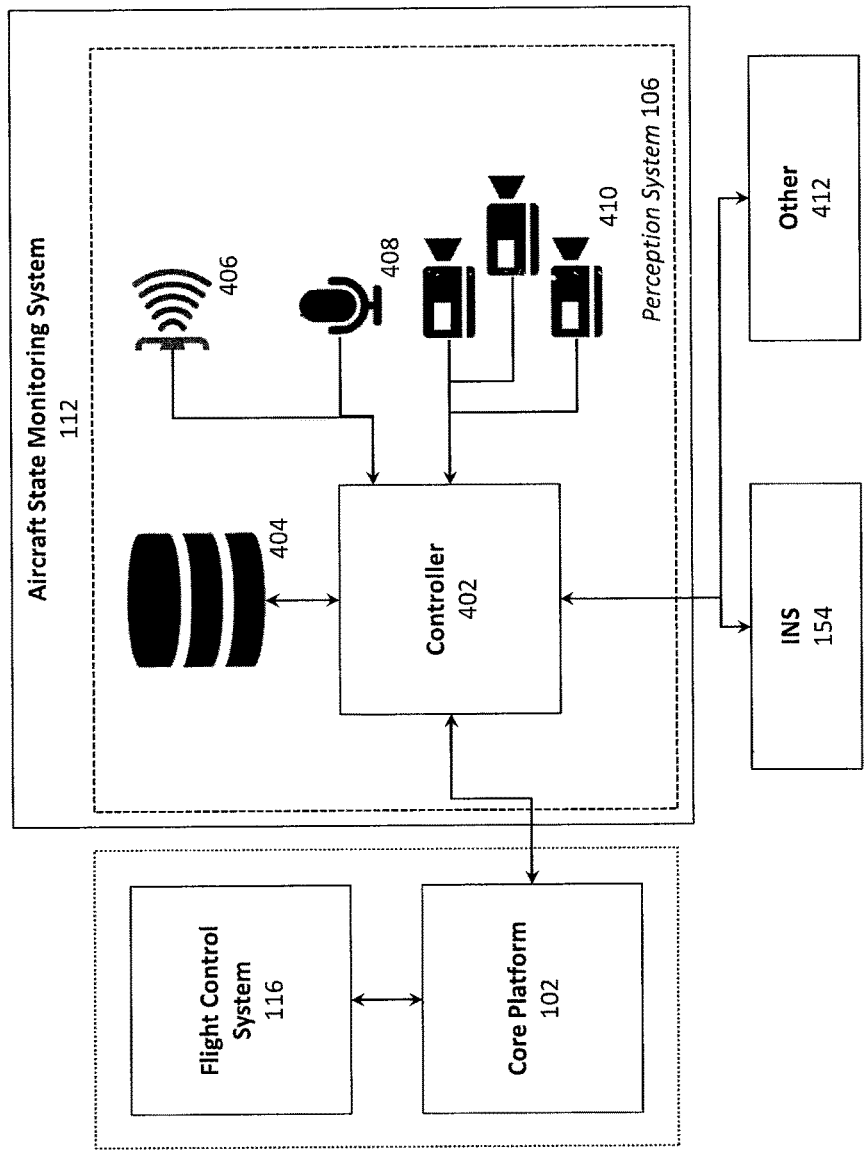
FIG. 4 illustrates a block diagram of an example perception system.

FIG. 4 illustrates an example perception system 106 operatively coupled with, inter alia, the core platform 102 (which is coupled to other subsystems, such as flight control system 116), the GPS/INS system 154, the aircrew health monitoring system 160, and any other input systems 412. The perception system 106 visually and/or acoustically monitors, inter alia, the cockpit instruments to generate flight situation data that can be used to derive the aircraft state from cockpit layouts, which may range from basic analog aircraft instruments to highly integrated, glass cockpit avionics suites. In addition to deriving physical state such as airspeed and altitude, the perception system 106 may also monitor instruments that are specific to aircraft systems such as fuel gauges and radios and provide secondary feedback about the status and positioning of the actuation system 108.

As illustrated, the perception system 106 may comprise a perception controller 402 that is operatively coupled with a database 404 and a plurality of sensors, such as cameras 410 (used for the vision system), microphone 408 (used for the acoustic system), and/or other sensors 406 (e.g., temperature sensors, positional sensors, inertial sensors, etc.). The perception controller 402 may be, for example, a processor configured to feed flight situation data to (or otherwise instruct) the core platform 102 based upon information received and manipulated information received from the plurality of sensors, the database 404, and external components, such as the GPS/INS system 154 and other input systems 412.

Vision System.

The perception system 106 may employ a monocular or stereovision system, possibly including motion capture markers, to continuously monitor the state of the aircraft by reading what is displayed on the cockpit instruments. In certain aspects, by comparing information about a scene from two vantage points, 3D information can be extracted by examining the relative positions of objects in the two panels. The vision system may be used to accurately monitor instruments (e.g., glass gauges, physical steam gauges, etc.) and switches, as well as their positions in a variety of lighting conditions and cockpit layouts and sizes. Using a stereovision system and/or markers also provides sensing to prevent collisions between any robotic components and the pilot.

The vision system may employ a suite of high-definition, stereo cameras and/or a LIDAR laser scanner. The system may be capable of recognizing data from all flight instruments and derive the state of switches knobs and gauges that display the state of aircraft specific systems (e.g., remaining fuel). It may also be capable of recognizing the state of the panel with enough resolution to detect minor changes that result from pilot actions. Machine vision algorithms on the perception system 106 computer 'read' the instruments (gauges, lights, wind correction angle panel, individual elements of the primary flight display or multi-function display in a glass cockpit) and mechanical items such as throttle levers, trim settings, switches, and breakers to provide a real-time cockpit state update to the core platform 102.

The perception system 106 may be capable of deriving the aircraft state from cockpit layouts ranging from basic analog aircraft instruments to highly integrated, "glass cockpit" avionics suites. Through the vision system, the requirement for a data feed from the aircraft is obviated, which permits/ increases portability across aircraft. However, when possible, the aircrew automation system 100 may also be coupled to an aircraft's data feed (e.g., through a data port). Further, using the application approach described for the core platform 102, different cockpit layouts can be addressed and understood using different underlying operation applications 202. For example, the aircrew automation system 100 may employ the gauge application 314 to derive the values displayed on the instruments, whether graphical dial (e.g., analog "steam" gauges or digital representations thereof) or a glass cockpit. This approach would also enable the aircrew automation system 100 to run operational applications that monitor, inter alia, weather radars, traffic displays, and terrain maps displayed in the cockpit.

In order to make aircrew automation system 100 portable, the process of rapidly learning a new cockpit layout and codifying subtle differences in location and scaling or unit of instruments is addressed by the perception system 106 design. For example, during the initial knowledge acquisition phase, the location and scale of instruments and switches can be encoded and verified for a particular aircraft, reducing the real-time task to the extraction of the position of the graphical dial (round dial) or number (glass cockpit), whether graphical dial gauges, CRT display, LCD, etc. The piece-wise planar structure of cockpit instrumentation enables the perception system 106 to construe the images (e.g., using Homography methods) and register it against the pre-mapped data generated during the initial knowledge acquisition phase. Accordingly, live imagery can be registered and compared against the previously annotated model, thereby greatly simplifying interpretation of the data.

Actuation System 108.

When desired, an actuation system 108 executes the actions commanded via the core platform 102 to guide the flight and overall operation of the aircraft. The aircrew automation system's 100 actuation system 108 executes the actions commanded by the core platform 102 to guide the flight and overall operation of the aircraft without interfering with the activities performed by the pilot. As illustrated in FIG. 1b, for example, the actuation system 108 may receive actuation commands and configuration data from the core platform 102, while sending to the core platform 102 status and response information generated by the actuation system 108.

Manned aircraft cockpits are designed for the human reach envelope and, therefore, all cockpit controls are reachable by a comparably sized robotic/mechanical manipulator. A manipulator capable of actuating every single switch, knob, lever and button on every single possible cockpit in high-G and vibration environments with the rapid execution required for emergency operation, however, would be expensive, heavy, and more invasive than what is desired for the aircrew automation system 100.

To more effectively achieve portability across aircraft, the aircrew automation system 100 may separate the actuation of primary flight controls (stick/yoke, stick, side-stick or collective, rudder pedals, brakes, and throttles) from the actuation of secondary flight controls (e.g., switches, knobs, rockers, fuses, etc.). This approach reduces the likelihood of designing a single point solution that becomes obsolete as aircraft evolve. Thus, the aircrew automation system 100 may employ a primary actuation system 108a and a secondary actuation system 108b to physically control the actuators in the cockpit. More specifically, the primary actuation system 108a may actuate the primary flight controls, while the secondary actuation system 108b may actuate the secondary flight controls, without obscuring the use of those controls by the pilot. The primary actuation system 108a and the secondary actuation system 108b are configured to collectively actuate all standard controls present on today's flight decks during flight operations.

As discussed below, the primary actuation system 108a focuses on actuating the primary flight controls (stick/yoke, stick, side-stick or collective, rudder pedals, breaks and throttles), while the secondary actuation system 108b focuses on actuating the controls that are not as easily accessed by the primary actuation system 108a, such as secondary flight controls (e.g., switches, knobs, rockers, fuses, etc.).

Primary Actuation System 108a.

Figure 5A:
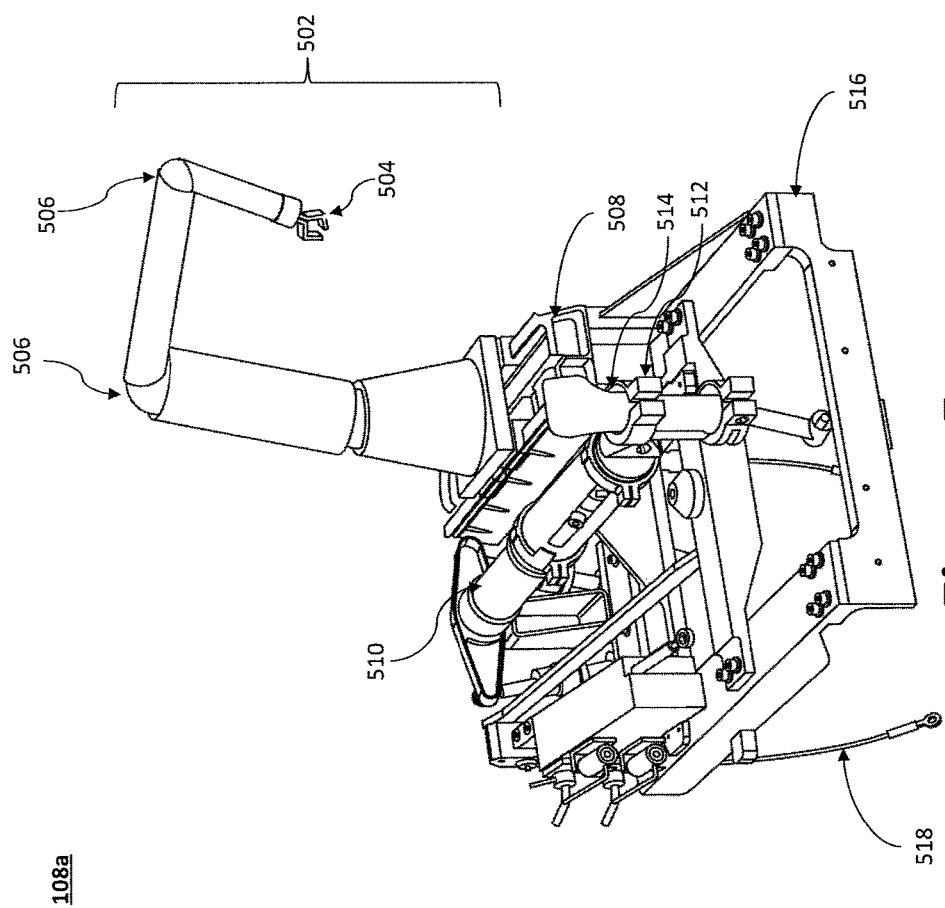
FIGS. 5a and 5b illustrate an example primary actuation system.
Figure 5B:
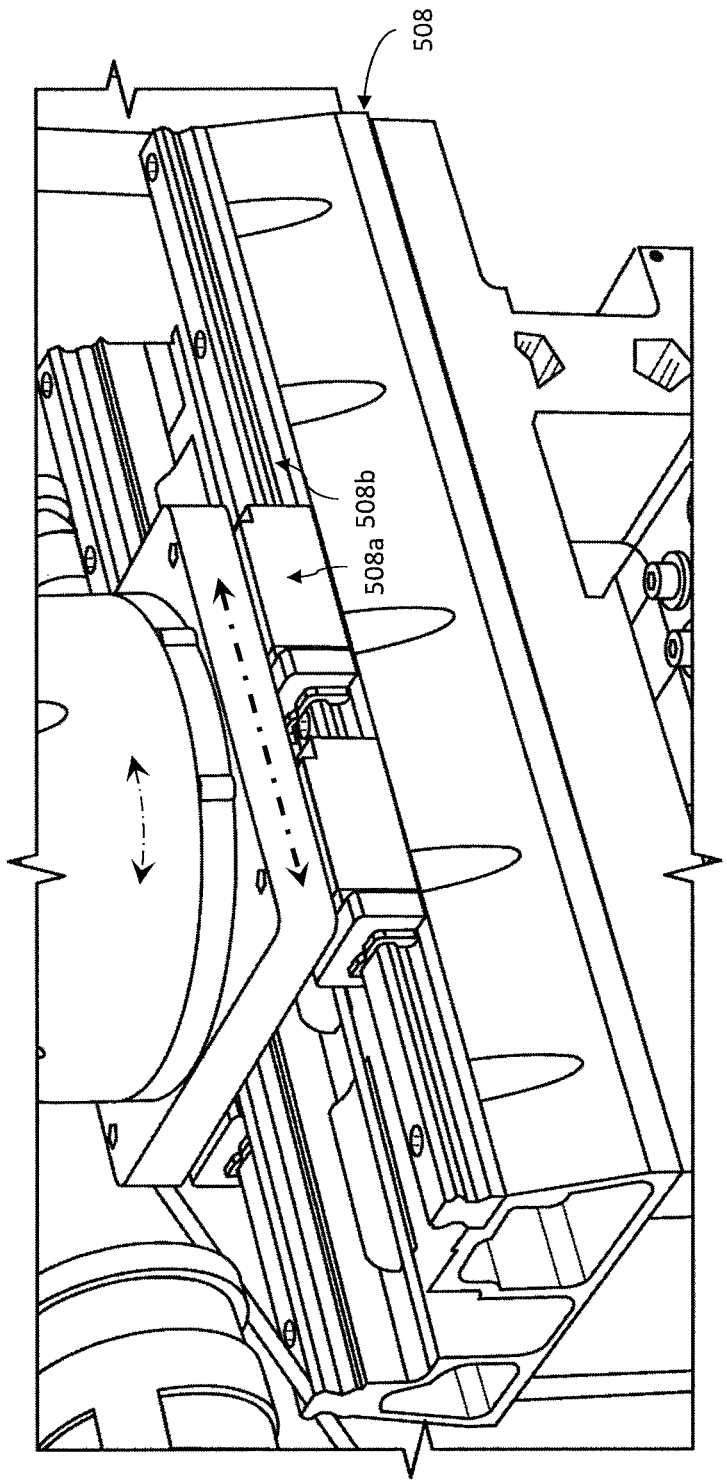

The primary actuation system 108a focuses on the set of controls necessary to safely operate the aircraft. As shown in FIGS. 5a and 5b, primary actuation system 108a include a frame 516 having an articulating arm 502 (e.g., a robotic appendage or "arm") and stick/yoke actuator 510 that actuates the primary flight controls (yoke, stick, side-stick or collective, rudder pedals, brakes, and throttles) and other, easy to reach controls. The actuators may be one or more of linear (straight line), rotary (circular), or oscillatory actuators, which may be driven through one or more of electrical, pneumatic, and/or hydraulic techniques.

The frame 516 may be sized and shaped to fit within the seat of a standard aircraft. To that end, the frame's 516 footprint should be about the same size as, or smaller than, an average human's "seated" footprint. The actuation system 108 may be fabricated using lightweight metals, metal alloys, and/or composite materials.

Stick/Yoke Actuator 510.

The stick/yoke actuator 510 may couple to and engage the aircraft's existing stick/yoke 514 using a stick/yoke gripper 512. The stick/yoke gripper 512 may be sized and shaped such that it is universal and can engage various forms of stick/yokes and/or control wheels. The stick/yoke actuator 510 may be configured to move the stick/yoke 514 forward, backward, left, right, and positions therebetween. The stick/yoke gripper 512 may further comprise one or more actuators for actuating buttons and/or switches positioned on the stick/yoke 514.

Articulating Arm 502.

The actuator-controlled articulating arm 502 may be sized, shaped, and configured to occupy the space typically occupied by a co-pilot's arms, thereby ensuring portability across aircraft. To enable movement in multiple degrees of freedom ("DOF") movement, the articulating arm 502 may comprise a plurality of arm segments (whether linear, curved, or angled) joined using a plurality of hinged or pivotal joints 506. The articulating arm 502 may comprise a gripper 504 at its distal end. The gripper 504 may be coupled to the articulating arm 502 via a multiple-DOF connection. The base of the articulating arm 502 may be rotatable and slideably coupled to the frame 516 via a movable base 508. For example, the articulating arm 502 may be coupled with an upper base 508a, which is slideably coupled with a lower base 508b, which may be secured to the frame 516. The upper base 508a may slide relative to the lower base 508b using, for example, a combination of rails and ball bearings. In certain aspects, the upper base 508a may slide relative to the lower base 508b along both the X- and Y-axis.

The articulating arm 502 can be equipped with an encoder (e.g., an 18-bit single-revolution rotational encoder) for each of its degrees of freedom to ensure exact positioning of the articulating arm 502. The encoders can be mounted at the motor, or at the joint itself (e.g., down-stream of any gearbox or other linkage). Internal clutches may be provided at each hinged or pivotal joint 506 such that the articulating arm 502 can be overpowered by the pilot if so desired, without damaging the articulating arm 502. In such a case, the aircrew automation system 100 may determine the position or location of the articulating arm 502 using the encoders.

The gripper 504 may be configured to couple, or otherwise engage, for example, throttle levers, etc. The gripper 504 may also provide force and pressure detection so as to allow the aircrew automation system 100 to estimate how a flight controls actuator is grasped and to adjust the motion to manipulate it properly. Once the motion is executed, the same feedback may be used to determine if the desired switch configuration has been achieved. In certain aspects, the articulating arm 502 may be fitted with an electronic device (e.g., a homing device) that enables it to find and hit a target.

Secondary Actuation System 108b.

Unlike the primary flight controls, which are generally located in the same vicinity across aircraft makes and types, the location of the secondary flight controls (e.g., avionics, switches, knobs, rockers, toggles, covered switches, fuses, etc.) is not as consistent or spatially contained from aircraft to aircraft.

The secondary actuation system 108b focuses on actuating the controls that are not as easily accessed by the primary actuation system 108a. For example, some switches may even be on an overhead panel directly above the captain's head, making it potentially difficult to manipulate them with a robotic arm (especially in turbulent flight conditions). Accordingly, some actuators may be allocated to the above described primary actuation system 108a, while others may be allocated to a self-contained, secondary actuation system 108b.

Figure 5C:
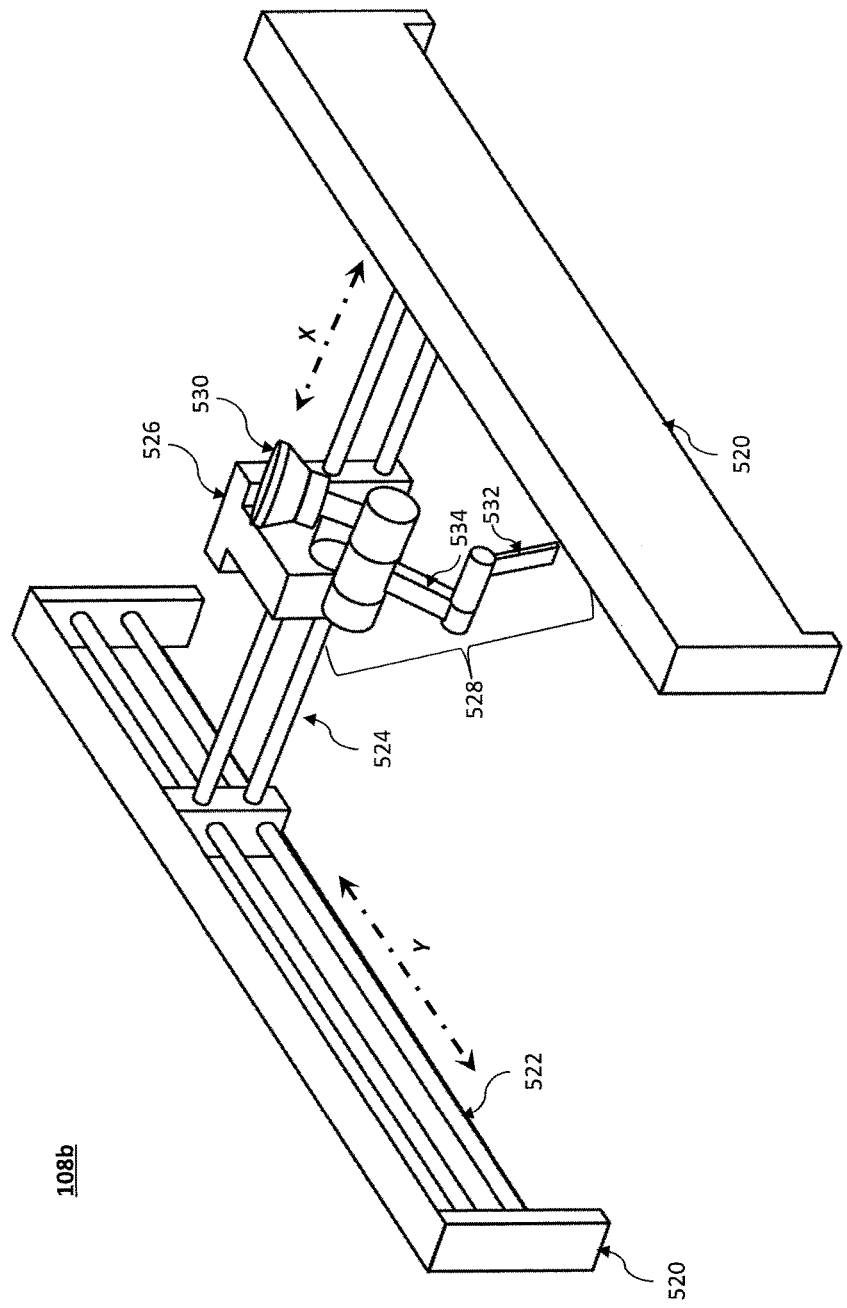
FIG. 5c illustrates an example secondary actuation system.

The secondary actuation system 108b may be provided in the form of an adaptable XY-plotter or gantry system mounted directly to the panel of interest and calibrated to the specific panel it is operating. The secondary actuation system 108b is preferably universal and resizable. An example XY-plotter is illustrated in FIG. 5c. The XY-plotter may comprise a square frame that serves as the rails 520 of the plotter, a rotatable multi-tool 528 with multiple interfaces (e.g., switch actuator 532 and knob actuator 530) capable of manipulating the controls of interest, and a control system that moves this multi-tool 526 within the frame along a Y-axis set of rails 522 and an X-axis set of rails 524.

When in use, the plotter moves the multi-tool 528 to the location, selects the correct manipulator interface, and manipulates the secondary flight control of interest. For example, the multi-tool 528 that can flip binary switches and/or covered switches using a switch actuator 532 and can twist knobs using a knob actuator 530. The switch actuator 532 and/or knob actuator 530 may be coupled to the multi-tool 528 via an articulating or rotating member, such as the rotatable switch arm 534.

When not in use, the multi-tool 526 may return to a home position (e.g., automatically navigate to a far corner) to prevent obstruction of the panel. The multi-tool 526 would be equipped with sensors (e.g., proximity sensors) such that it can move out of the way when it detects the pilot's hands. During the initial set-up of the plotter on a new aircraft, the location, type, and position of the secondary flight control panel may be encoded. Once a particular secondary flight control panel is encoded, the configuration can be saved to the aircraft data structure 208 and loaded when aircrew automation system 100 is installed in the same aircraft, or the same type of aircraft. In certain aspects, additional actuators may be provided to actuate controllers that are positioned in, for example, the foot well of the cockpit, such as foot pedals (e.g., brake and/or rudder pedals). While the secondary actuation system 108b is generally described as a gantry system, an articulating arm (akin to the arm of the primary actuation system 108a) may be employed for accessibly to secondary flight controls.

Aircrew Health Monitoring System 160.

Figure 6:
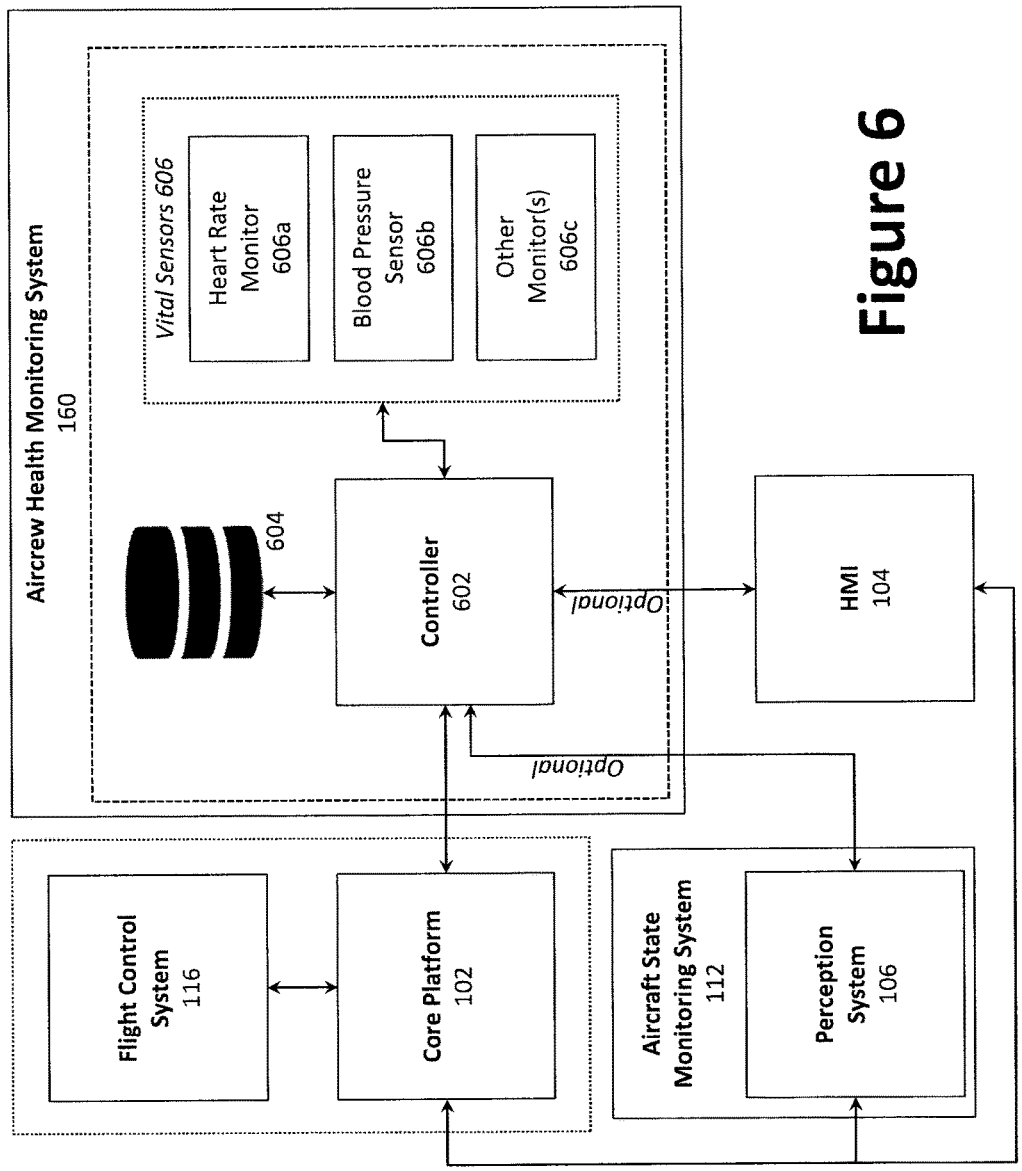
FIG. 6 illustrates an example aircrew health monitoring system.

FIG. 6 illustrates an example aircrew health monitoring system 160 to monitor one or more physiological states and/or behavioral states of the aircrew (e.g., the primary pilot/captain, co-pilot, etc.). The aircrew health monitoring system 160 may be operatively coupled with, inter alia, the core platform 102 (which is coupled to other subsystems, such as flight control system 116), the HMI system 104, and the perception system 106. As illustrated in FIG. 1b, for example, the aircrew health monitoring system 160 may receive commands and configuration data from the core platform 102, while sending to the core platform 102 aircrew physiological/behavioral information (e.g., aircrew health data) gathered by the aircrew health monitoring system 160 or otherwise collected by the aircrew health monitoring system 160.

As illustrated in FIG. 6, the aircrew health monitoring system 160 may comprise a health controller 602 that is operatively coupled with a memory device 604 and a plurality of vital sensors 606. The health controller 602 may be, for example, a processor configured to dynamically feed aircrew health data (i.e., representing physiological states and/or behavioral states) and/or commands (e.g., auto-land and auto-descent commands) to the core platform 102 based at least in part on information received from the plurality of sensors 406, the memory device 604, the HMI system 104, the perception system 106, etc. The communication links between the aircrew health monitoring system 160 and each of the HMI system 104 and the perception system 106 may be an indirect connection via the core platform 102 and/or an optional direct connection (which may be a redundant connection).

The vital sensors 606 may include biosensors and/or mechanical sensors positioned on or adjacent the aircrew member being monitored. The vital sensors 606 may include, inter alia, heart rate monitors 606a, blood pressure sensors 606b, and other vital monitors 606c, such as glucose monitoring; cardiovascular monitoring and event recording; neurological monitoring (e.g., electroencephalogram (EEG)) tests; and sleep monitoring devices.

The vital sensors 606 may be embodied as wearable sensors to be worn by the aircrew members, each having a unique identification number that can be correlated with a specific aircrew member. For example, wearable vital sensors may be provided as a wrist band, chest band, head bands, or other devices, such as garments, hats, socks, shoes, eyeglasses, wristwatches, headphones, and even portable user devices (e.g., the aircrew member's portable computer, portable digital assistant (PDA), smart phone, etc.).

The aircrew health monitoring system 160 may employ wireless devices to mitigate any physical restrictions imposed on the aircrew. For example, the vital sensors 606 may wirelessly communicate with the health controller 602 and/or the core platform 102 via one or more wireless transceivers. The one or more wireless transceivers may be configured to communicate using one or more wireless standards such as Bluetooth (e.g., short-wavelength, Ultra-High Frequency (UHF) radio waves in the Industrial, Scientific, and Medical (ISM) band from 2.4 to 2.485 GHz), near-field communication (NFC), Wi-Fi (e.g., Institute of Electrical and Electronics Engineers' (IEEE) 802.11 standards), etc.

The memory device 604 may generate a database of historic aircrew health data for each aircrew member during a flight. The historic aircrew health data and associated trends may be used by the health controller 602 to detect and/or predict health events (e.g., loss of consciousness, heart attack, etc.). In certain aspects, historic aircrew health data for each aircrew member may be loaded to the memory device 604. For example, upon aircrew shift change, the knowledge acquisition system 114 and/or the aircrew health monitoring system 160 may perform predefined activities to determine aircrew health and develop and overview of the aircrew health (e.g., per member). In certain embodiments, historic health data for each aircrew member to be monitored may be loaded by the aircrew upon starting a flight or a work shift. For example, the aircrew health monitoring system 160 may access and extract historic aircrew health data from a portable user device (or other device) associated with each aircrew member. The aircrew health monitoring system 160 may notify the pilot of any anticipated health issues based on, for example, predictive models and the historic aircrew health data.

Auto-Landing Procedure.

Commercial aircraft, such as the Boeing 737, often include an auto-landing controller to provide limited auto-landing capability. The auto-landing controller enables the aircraft to perform a landing to land at a touchdown location (e.g., a runway or another location deemed appropriate for landing the aircraft) without requiring direct interaction with certain of the primary flight controls. Existing auto-landing controllers, however, still require operation of other flight controls from within the aircraft cockpit. In cases where either the pilot or co-pilot is incapacitated (or otherwise unable to perform), the remaining pilot (if available) must perform the complete landing solo, which is intensive and requires the remaining pilot to initiate the proper automatic controls and to set a variety of secondary flight controls and systems (e.g., the landing gear, flaps, etc.). Therefore, the aircrew automation system 100 may be further configured to perform, during an emergency, a descent and landing procedure in an aircraft equipped with an auto-landing controller. The aircrew automation system 100 may perform the auto-landing procedure using touch and/or vision sensing (e.g., via the perception system 106). While touch sensing (i.e., detecting touch using a force-sensing sensor) is not strictly required to perform a landing, touch sensing improved system robustness and error checking.

As can be appreciated, the actuation system 108 of the aircrew automation system 100 must be capable of physically manipulating the various flight controllers. Because the auto-landing procedure is most applicable to emergency descent and landing situations, the actuation system 108 may be configured to quickly couple to the various flight controllers in lieu of the incapacitated pilot. To that end, minor modifications to cockpit controls may be warranted to improve interaction between the actuation system 108 and the various flight controllers, such as situations where the existing flight controller difficult to access via the actuation system 108. For example, fast-installable brackets may be non-invasively attached to levers (e.g., landing gear levers) to enable the actuation system 108 to manipulate (e.g., push/pull) the lever. To that end, a bracket (e.g., a 3d-printed/additive manufactured bracket) may be available to pilot in the cockpit to enable the actuation system 108 to manipulate, for example, a landing gear lever.

The present aircrew automation system 100 may be configured to perform a specific auto-landing procedure for emergency descent and landing of an aircraft. For example, the aircrew automation system 100 may be integrated with an aircraft that already contains a limited auto-landing infrastructure (e.g., control of primary flight controls and glide slope), but that which still requires interaction with the cockpit to fully execute the auto-landing. One of numerous aircraft that would benefit from an auto-landing procedure is the Boeing 737, although the auto-landing procedure is equally applicable to other aircraft that include a limited auto-landing infrastructure. As will be discussed below, the auto-landing procedure may be initiated in response to an auto-land trigger, which may be automatically (or manually) generated through aircrew monitoring to identify pilot incapacitation.

The aircrew automation system 100 may further enable voice interaction between the cockpit and the air traffic control tower via the communication system 122. For example, the aircrew automation system 100 may assess the situation and relay messages describing the situation to the air traffic control tower. In another example, the aircrew automation system 100 may relay information from the remaining aircrew (e.g., via the HMI system 104 or the perception system 106—e.g., via the speaker/microphone 408) to the air traffic control tower describing the situation. The information communicated to the air traffic control tower may further include health information about the pilot (e.g., via the share icon 342). The aircrew automation system 100 may glean information about the flight state using machine vision via the perception system 106. For example, some procedures must not be performed until reaching critical flight state and verify important steps such as setting the flaps.

Therefore, during an auto-descent and auto-landing procedure, for example, the aircrew automation system 100 may perform a number of steps typically performed by a pilot. For example, the aircrew automation system 100 may be configured to: (1) operate an autopilot panel; (2) operate flaps and autopilot panel in a coordinated manner to safely reduce airspeed; (3) identify the glide slope to a touchdown location and perform landing procedures in coordination with this signal; (4) manipulate the flight management system to generate a landing route; (5) set the autobrake; (6) set the landing gear; (7) identify a landing/wheels on the ground condition; (8) operate the throttle and reverse thrusters to aid in braking on the ground; (9) set the transponder to note an emergency; and/or (10) communicate to air traffic control the state and intention of the aircraft.

Auto-Land Trigger.

Promptly and accurately triggering the aircrew automation system 100 to generate a command to perform the auto-descent and/or auto-land procedure(s) in an emergency is imperative. Accordingly, an aircrew health data feed from aircrew health monitoring system 160 to the core platform 102 may further include an auto-descent and/or auto-land command to initiate the auto-descent and auto-landing procedures upon the occurrence of an auto-land trigger. The auto-land trigger may be, for example, a direct command from the operator (e.g., the pilot or other aircrew member) or generated automatically (e.g., by the health controller 602) based at least in part on data received from the vital sensors 606, the perception system 106, and/or, the HMI system 104. In certain aspects, such as in the case of a direct command from the pilot, the direct command may be instead provided directly to the core platform 102 via the HMI system 104 (whether orally or via a user input device, such as a touch screen display), thereby bypassing the aircrew health monitoring system 160.

The health controller 602 may determine that the pilot is incapacitated using the vital sensors 606 coupled to the pilot, in which case the health controller 602 may communicate the auto-land command to the core platform 102 when a health parameter of the pilot deviates from a predetermined value or range of acceptable values. For example, the vital sensors 606 may provide cardiac parameters indicative of a heart attack, stroke, death, etc., in which case the auto-land command is automatically communicated to the core platform 102. The health controller 602 may also determine that the pilot is incapacitated using the perception system 106. Indeed, the perception system 106 may employ one or more cameras 410 and/or microphones 408 to monitor the pilot's movements (or lack thereof) and voice (or other sounds).

The health controller 602 may employ the one or more cameras 410 of the perception system 106 to determine whether the pilot's body posture is poor (e.g., hunched over/slouched) or the pilot's apparent motor coordination is off (e.g., erratic, sluggish, unable to manipulate the controls, etc.), in which case the health controller 602 may determine that the pilot is incapacitated (e.g., unconscious, dead, and/or under the influence of drugs or alcohol).

The one or more cameras 410 may also monitor the pilot for loss of focus or gaze, in which case the one or more cameras 410 may employ eye-tracking techniques to monitor, for example, pupil movement, pupil size, and/or point of gaze. Accordingly, a camera 410 may be configured to focus on one or both of the pilot's eyes to monitor and/or record pupil/eye movement as the pilot performs tasks. For example, the camera 410 may be directed to the center of the pupil and may use infrared/near-infrared non-collimated light to generate corneal reflections, where the vector between the pupil center and the corneal reflections can be used by the health controller 602 to compute the point of gaze. The health controller 602 may determine that the pilot is incapacitated because of loss of focus or gaze if, for example, the pilot continues to stare at a single point for a predetermined period of time or does not look at the cockpit instruments within a predetermined period of time.

The health controller 602 may employ the microphones 408 of the perception system 106 to determine whether the pilot's voice becomes slurred (based on a comparison to earlier voice samples, which may be stored to a database of the memory device 604), for example, the health controller 602 may determine that the pilot is incapacitated (e.g., semi-unconscious and/or under the influence of drugs or alcohol). The microphones 408 may further be configured to receive commands or requests for help from the pilot using voice recognition.

The health controller 602 may employ the HMI system 104 to determine whether poor interaction existed between the pilot and the HMI system 104, such as during checklist procedures. For example, the health controller 602 may compare pilot interaction during a checklist procedure with historic pilot interaction data for the same pilot during prior checklist procedures. If the pilot's interactions with the HMI system 104 deviates from the historic pilot interaction data by more than a predetermined deviation (e.g., a percent deviation), the health controller 602 may determine that the pilot is incapacitated. As noted above, the aircrew health monitoring system 160 may notify the pilot of any anticipated health issues based on, for example, predictive models and the historic aircrew health data.

Auto-Land Termination.

In certain aspects, the auto-landing procedure may be terminated or cancelled if the health controller 602 determines in error that the aircrew member is incapacitated. To validate termination of the auto-landing procedure, the health controller 602 may require a termination input from an aircrew member who is not the aircrew member that was determined to be incapacitated. To terminate the auto-landing procedure, the health controller 602 may further require an authentication input from the aircrew member who is not the aircrew member that was determined to be incapacitated, such as pin number, access code, password, fingerprint, badge ID (e.g., RFID badge), retinal scan, etc. For example, if the health controller 602 determines that the pilot is incapacitated, the co-pilot may terminate the auto-landing procedure if he or she deems that the pilot fit to fly the aircraft, in which case the co-pilot may enter a password/pin number (or other identifying information) and terminate the auto-landing procedure via, for instance, the HMI system 104.

Knowledge Acquisition System 114.

The knowledge acquisition system 114 gathers and/or generates a knowledge base necessary to enable the aircrew automation system 100 to determine aircraft specific information. This includes knowledge of aircraft performance characteristics, limitations, checklists, and procedures (including emergency procedures), and criteria that define contingencies in the aircraft. The data may be derived from a combination of encoded data (e.g., from manuals, pilot briefings, pilot operating handbook) and data acquired in flight (e.g., via sensors), which supports off-line machine-learning and trend analysis. The date to be encoded may be loaded in .xml format that describes the contents of procedures and the flow of tasks both within and between procedures.

As illustrated in FIG. 1b, for example, the knowledge acquisition system 114 may receive operational commands from the core platform 102, while sending to the core platform 102 configuration data and status and response information generated by the knowledge acquisition system 114.

The operation of the knowledge acquisition system 114 may be generally divided into three processes, including, for example, aircraft system modeling, procedure codification, and aerodynamic modeling. The aircraft system modeling process provides the aircrew automation system 100 with information about the available onboard systems and how the onboard systems are configured, actuation limits, etc. The procedure codification process provides the aircrew automation system 100 with information about aircraft operation in normal and non-normal situations. Procedure codification may include, for example, the codification of checklists. Finally, aerodynamic modeling process provides the aircrew automation system 100 with information about flying the aircraft and what performance to expect for a given aircraft type and configuration.

During the knowledge acquisition phase, the conditions under which a situation is considered an anomaly or contingency must also be established. These conditions will frequently be discrete, such as an engine over-speed or the exceedance of an airspeed limit. Using machine learning, the aircrew automation system 100 can fine-tune its aerodynamic and control models by observing a series of in-flight maneuvers flown by the pilot. This information includes flight dynamics data, operational limitations, procedures, aircraft systems, and layouts as well as other related data. In addition to written information, the aircrew automation system 100 may also codify information based on past events and experience of more experienced pilots. Machine learning enables the knowledge acquisition process to be performed efficiently and quickly.

Using aircrew automation system's 100 perception system 106 and actuation system 108, the instruments and controls in a plane cockpit or a realistic simulator are monitored as a pilot goes through the motions of a typical flight profile. Observing the pilot's actions allows the aircrew automation system 100 to learn directly from the pilot and imitate the smooth, expert control for a given operation. This process benefits from the fact that flight operations are highly structured in what is to be done in a given situation—machine learning then enables the codification of how something is to be executed.

The population of aircraft data structure 208 may be accomplished using the Extensible Markup Language ("XML"). More specifically, a XML data structure may be employed that comprises a set of fields and data trees that, when populated, allow the core platform 102 to configure and operate an aircraft. In certain aspects, the aircrew automation system 100 may employ natural language interpretation of flight documents and/or a software tool that enables a human to enter the data efficiently and accurately.

In certain aspects, a set of airplane agnostic features may be generated and coded. For example, procedures like landing gear retraction, engine out procedures on multi-engine aircraft, and stall recovery are similar across many types of aircraft and will need only minimal modification for a particular airframe. Moreover, basic airframe limitations (such as never exceed speeds) need only be entered as specific numbers and can be entered from flight manuals in a nominal period of time.

Procedure Editor.

The aircraft specific information may be gathered during a transition period using, for instance, written documentation (e.g., pilot operating handbook, maintenance manual, etc.) as well as through direct monitoring of aircraft operations. The output of this knowledge acquisition process is the aircraft data structure 208, which is described above with regard to the core platform 102. Contained in this aircraft data structure 208 may be operational procedures, available systems and their designs, cockpit layout, and all other information necessary for safe operation of the aircraft. In certain aspects, an aircrew automation software development kit may allow a software/flight controls engineer to specify, code, and unit-test one aircraft subsystem (e.g., electrical or hydraulic) per day. The aircrew automation software development kit can provide tools for turning the flight manual's procedures into state machines compatible with Matlab State Flow and Simulink, which can then auto-code the procedures in C for inclusion in the core platform 102. The aircrew automation software development kit may also generate test code for the unit-level as well as interfaces for testing to the core platform 102. For example, the procedure editor may provide a list of tasks where the pilot may select whether the aircrew automation system 100 or the pilot is responsible for a given task on the list.

Knowledge Acquisition of Flight Control.

A first step in knowledge acquisition of flight control uses the Athena Vortex Lattice ("AVL") method to generate the mathematical model in the form of non-dimensional stability derivatives that is used and refined during the flight with the pilot. Once the primary flight control mechanisms are calibrated, the system ID trainer application may be used to perform a sequence of flight maneuvers designed to identify specific stability derivatives. The data is automatically processed into updated stability derivatives for use in the controller. The controller may employ an auto-tuner. The same updated stability derivatives are used in a 6-DOF simulation as a validation step that the controllers perform adequately prior to flight. An additional benefit of performing knowledge acquisition of flight control is that it enables the refinement and incorporation of a great deal of formal procedural knowledge. Although the procedures lay out the individual steps, fine detail on how such steps are to be executed may be missing (e.g., how long to wait between steps or how sharply to increase throttle).

Reverse Engineer of Aircraft Flight Performance Characteristics.

Aircraft performance characteristics that can be measured through on-board data-acquisition units are generally considered proprietary by the aircraft and avionic manufacturers. This information can be utilized for flight simulations, aircraft health monitoring, aircraft development, and much more. Currently, third parties wanting to utilize the on-board data acquisition are restricted by its proprietary nature. This restriction has only been partially been overcome through the use of stand-alone aircraft sensor suites. These commercially available sensor suites only measure a fraction of the data available through cockpit instrumentation and pilot inputs. However, because the aircrew automation system 100 utilizes a variety of sensors to determine the aircraft flight performance characteristics, it effectively reverse engineers the air vehicle performance characteristics. The aircrew automation system 100 collects aircraft information through a combination of stand-alone sensors, data capture through images of cockpit instrument, and input controls.

EXAMPLES

Aspects of the present disclosure may be illustrated through the following example flight plan and emergency procedures, which illustrates how aircrew automation system 100 may interact with the pilot, execute a flight plan, execute flight operational tasks, and respond to contingencies during system engagement and takeoff, flight plan engagement, anomaly detection & handling, and emergency descent/landing procedures. The present teachings, however, should not be limited to those used in these examples.

System Engagement and Takeoff.

The pilot gets into the left seat of an aircraft, fastens the seat belt, positions the human-machine interface 126 comfortably at his side, and activates the aircrew automation system 100 application. The application boots and runs through a series of power-on diagnostics and the mechanical interfaces power up and calibrate. A message may be displayed upon the human-machine interface 126 confirming a successful test and queries the pilot to confirm engagement of aircrew automation system 100. The pilot selects the day's flight plan via the applications tab 334. The aircrew automation system 100 may be used for checklist monitoring. The pilot selects engine start, and aircrew automation system 100 may begin a sequence of engine start actions, asking for final confirmation before actually starting. Meanwhile, the pilot may call the tower for clearance and receives a flight plan to the training area.

When engine start is complete, the aircrew automation system 100 may report success to the pilot and report, for example, "ready to taxi," (either audibly or via the human-machine interface 126). The pilot calls for a taxi clearance and upon hearing it, the aircrew automation system 100 transcribes the taxi clearance and displays it to the pilot for confirmation. The pilot then hits the "taxi via clearance" button on the application and aircrew automation system 100 taxis to the assigned runway while the pilot monitors for traffic. When at the runway threshold, the pilot verbally commands the aircrew automation system 100 to perform a pre-takeoff check and the system completes all necessary checks, prompting the pilot to manually double-check critical items, such as flight controls. For example, the aircrew automation system 100 may monitor the human operator's execution of a checklist, and output "checklist complete" or identify a flight plan or error.

Upon receiving further clearance, the pilot then commands the aircrew automation system 100 to guide the aircraft to line-up and wait, and then ultimately takeoff. The aircrew automation system 100 pushes the throttles forward via the primary actuation system 108a, visually checks engine and cockpit indicators via the perception system 106, calls out speeds via the HMI system 104, and rotates at the speed appropriate to the current weight, balance, and density altitude. The pilot keeps his hand on the stick/yoke 514 to confirm aircrew automation system's 100 inputs and retain his muscle memory. The aircrew automation system 100 confirms aircraft performance according to current conditions and reports any deviation from expected climb rate. The pilot's workload is reduced by the aircrew automation system 100 during climb, enabling more heads-up time (i.e., eyes forward, not on the instruments) to look for traffic in the busy airspace. The aircrew automation system 100 may also provide experienced pilot advice for a given checklist, aircraft, or location. For example, in a particular airport, the aircrew automation system 100 may instruct the human operator with airport specific tips, such as "steep departure angle from this runway."

Flight Plan Engagement.

At the top of climb, the aircrew automation system 100 levels off the aircraft and adjusts trim and power settings while heading to the first waypoint in the flight plan. During cruise, the aircrew automation system 100 continues to visually monitor all cockpit displays, constantly comparing engine and aircraft performance against expected values and alerting the pilot to any deviations.

The aircraft arrives at the training area and begins the day's flight plan. During the flight plan, however, the aircraft enters a towering cumulus cloud, where instrument meteorological conditions ("IMC") conditions are at below freezing temperatures. The pilot requests and receives clearance from the ground, via an internet relay chat ("IRC") chat window on the human-machine interface 126, to climb to 24,000 feet to get above the weather. In certain aspects, the aircrew automation system 100 request clearance from the ground.

Anomaly Detection & Handling.

After a period of time, the aircrew automation system 100 may detect that given the climb, the indicated airspeed is slowly deviating from its modeled airspeed for these pitch and power settings, indicating lower than expected values. This is an indication that the pitot heater has failed and the pitot tubes have iced up. The pilot has fewer than 100 hours flying the aircraft and is not aware that pitot heaters in this model are known to be unreliable. The pilot has not yet noticed that the airspeed indicator is trending below nominal.

The aircrew automation system 100, however, recognizes that the airspeed data is anomalous to the rest of the flight data and its internal flight dynamics model, and aurally warns the pilot "airspeed indicator fault." While the pilot recognizes that the airspeed information is currently unreliable, he is unsure as to whether the aircraft is flying faster or slower than the indicator shows.

Drawing on a database of prior anomalies, the aircrew automation system 100 presents a set of procedural options and highlights the minimum safe altitude for the area (e.g., 8,000 ft). The pilot chooses the most conservative option, which results in wings level, pitch, and power descent to a lower altitude (e.g., 10,000 ft). The aircrew automation system 100 eases back on the power, pitches slightly down, and commences the descent. While descending through 15,000 feet the pitot tubes again come online. Once stable at 10,000 feet, the aircrew automation system 100 holds the aircraft straight and level while the pilot assesses the situation prior to returning to the flight plan.

Upon competition of the day's flight plan, the aircrew automation system 100 may execute an automatic landing procedure. For example, the aircrew automation system 100 may navigate the aircraft to a predetermined waypoint, where the aircraft may commence its initial descent. During the descent, the aircrew automation system 100 may monitor the flight conditions and locate the runway. Upon final approach, the aircrew automation system 100 may slow the aircraft down and ultimately land the aircraft. If the aircrew automation system 100 determines that landing is not feasible (e.g., an obstruction or unacceptable flight conditions), the aircrew automation system 100 may commence a missed approach routine or other contingency routine. For example, the aircrew automation system 100 may retry landing at the same location or navigate the aircraft to an alternative landing location. An example system for landing an aircraft at an alternative landing location is disclosed by commonly owned U.S. Patent Publication No. 2015/0323932, titled "Autonomous Cargo Delivery System."

Pilot Incapacitation Event.

In addition to aiding a human pilot during take-off through cruise, the aircrew automation system 100 may perform one or more automatic sequences to address a pilot incapacitation event caused by, for example, cabin depressurization at high altitude. For example, the aircrew automation system 100 may perform an auto-descent procedure and, once at a predetermined altitude and location, perform an auto-land procedure. The pilot may use voice commands to instruct the aircrew automation system 100 to perform tasks during the various stages of flight, including during a pilot incapacitation event. The perception system 106 may observe operations performed by both the aircrew automation system 100 and the human pilot(s).

As discussed above, the aircrew automation system 100 can operate and monitor the aircraft's flight controllers and interfaces through the perception system 106 and the actuation system 108. To that end, the aircrew automation system 100 can operate, for example, altitude, heading and airspeed (which may be controlled through the autopilot), transponder code, the flight management system, autobrake, landing gear, flight surfaces (e.g., flaps), throttle reverse thrusters. Throughout the processes, the aircrew automation system 100 may perform checklists to verify that flight procedures are correctly followed whereby checklist items can be checked off by the pilot or by the perception system 106, which is configured to observe the state of the aircraft.

Figure 7:
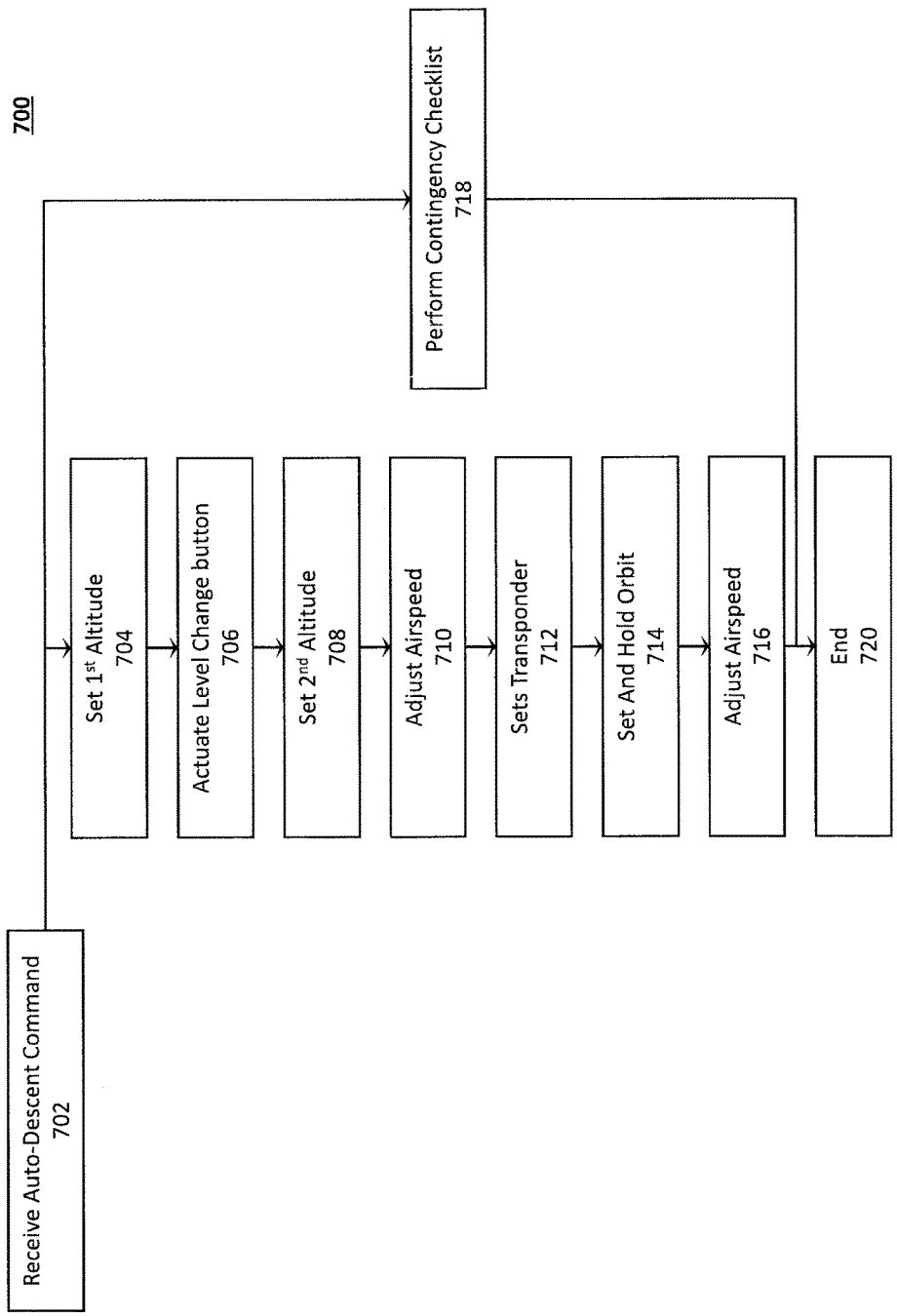
FIG. 7 illustrates an example emergency descent procedure.

FIG. 7 illustrates an example emergency descent procedure 700. The example emergency descent procedure 700 demonstrates the ability of the aircrew automation system 100 to operate the aircraft in the event of pilot incapacitation. In this demonstration, the emergency descent procedure 700 may begin at step 702 upon receiving an auto-descent command or indication of pilot incapacitation. In certain aspects, a single command (e.g., an auto-land command) may be used to trigger the aircrew automation system 100 to perform both the emergency descent procedure 700 and auto-land procedure 800, described below. While the emergency descent procedure 700 and auto-land procedure 800 are illustrated as having a particular combination of steps, one of skill in the art would appreciate that fewer or additional steps may be implemented. In certain aspects, one or more steps may be performed in parallel. Further, one or more steps may be optional and omitted from the emergency descent procedure 700 and/or the auto-land procedure 800, or performed separately and/or upon request from an operator. In some aspects, one or more steps may be conditional, such that execution of the one or more steps may be contingent upon predetermined requirements and/or conditions. Moreover, the order in which the steps are cycled may be rearranged depending on the needs of the operator.

The auto-descent command may be triggered upon detection of pilot incapacitation (e.g., via the aircrew health monitoring system 160), after which aircrew automation system 100 will operate the aircraft. In another example, the auto-descent command may be triggered by a pilot voice command. For example, the co-pilot may recite a predetermined phrase (e.g., "Begin Descent Checklist") to signal to the aircrew automation system 100 that the pilot is incapacitated. At step 704, the aircrew automation system 100 sets the altitude to a first altitude (e.g., 20,000 feet).

At step 706, the aircrew automation system 100 actuates a flight controller to initiate the descent using the actuation system 108. For example, in a Boeing 737, the secondary actuation system 108b may be used to push the "Level Change" button to initiate the descent. After which, the aircraft will descend from a cruising altitude, for example, to the first altitude.

At step 708, the aircrew automation system 100 sets the altitude to a second altitude (e.g., 10,000 feet). For example, the secondary actuation system 108b may be used to again push the "Level Change" button to initiate a second descent. After which, the aircraft will begin its descent from the first altitude to the second altitude.

At step 710, the aircrew automation system 100 may adjust the airspeed of the aircraft to a predetermined airspeed. The predetermined airspeed may be selected to more quickly descend to the second altitude. For example, the aircrew automation system 100 may increase the airspeed of the Boeing 737 to 0.82 Mach (~546 knots or ~630 miles per hour), which is the fastest allowable descent rate using the autopilot.

At step 712, the aircrew automation system 100 sets the transponder to emergency code 7700. By setting the transponder to the emergency code of 7700, all air traffic control facilities in the area are immediately alerted that the aircraft has an emergency situation. The aircrew automation system 100 may further indicate to the air traffic controller the type (or specifics of) of the emergency situation. For example, the aircrew automation system 100 may indicate that the pilot is incapacitated and, in certain circumstances, may further communicate the pilot's vitals to the ATC so that emergency medical personal on the ground can plan accordingly.

At step 714, the aircrew automation system 100 programs the flight management system to set and hold an orbit (e.g., a holding pattern) around its current position. The aircrew automation system 100 may hold the orbit at or near its current position until the aircraft has achieved the second altitude, which may be monitored using machine vision from the perception system 106.

At step 716, the aircrew automation system 100 may again adjust the airspeed of the aircraft to a predetermined airspeed. For example, the aircrew automation system 100 may decrease the airspeed of the Boeing 737 to 0.375 Mach (~250 knots or ~287 miles per hour) to circle in place at lower airspeed.

In parallel with steps 704 through 716, the perception system 106 may perform the contingency checklist of step 718. For example, the perception system 106 may observe the actions of the aircrew automation system 100 during steps 704 through 716 to check items off a contingency checklist (e.g., to ensure that the aircrew automation system 100 has performed the necessary actions) as they occur, or shortly thereafter. For example, the perception system 106 may verify each step before the emergency descent procedure 700 may proceed to the next step. In the event that a step is not observed by the perception system 106, subject to operator settings, the perception system 106 may communicate with the core platform 102 to communicate to the actuation system 108 that the step was not performed correctly (or at all). In certain aspects verification cannot be perform dynamically, but after a delay, which may be caused by the time needed for the perception system 106 to calculate the change (e.g., at update rates of 1 to 100 Hz speed). Additionally, delay may be caused by the dynamics of the aircraft taking time to respond to the input command and/or because the actuation system 108 is visually occluding the cameras 410 (e.g., immediately after performing a manipulation when the actuation system is still hovering adjacent the button).

The emergency descent procedure 700 may end at step 720 when the aircraft is circling in place the second altitude (or another desired altitude). The aircraft may circle in place at the second altitude until an auto-land command is received.

Auto-Land Procedure.

Figure 8:
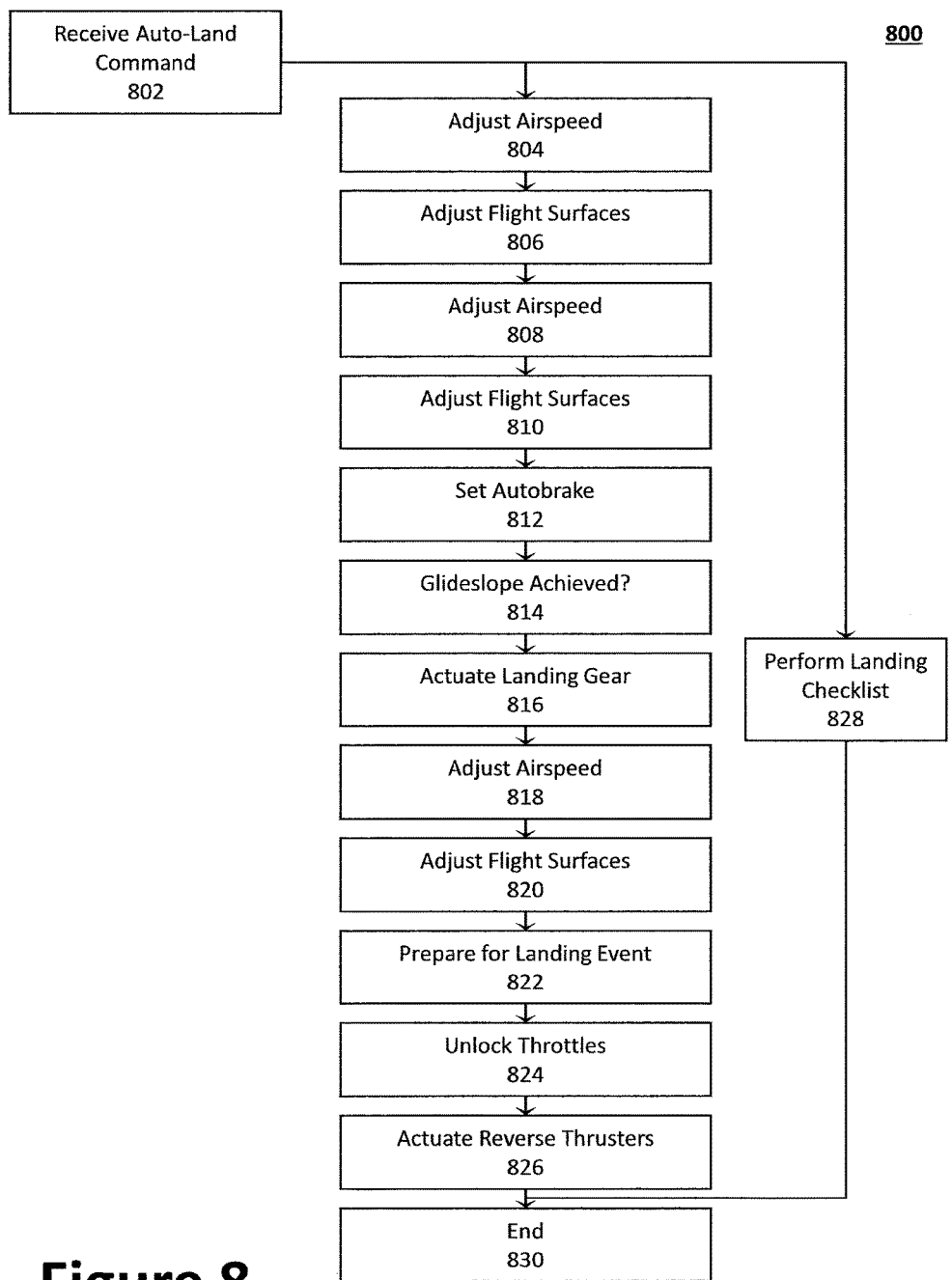
FIG. 8 illustrates an example auto-land procedure.
Figure 9:
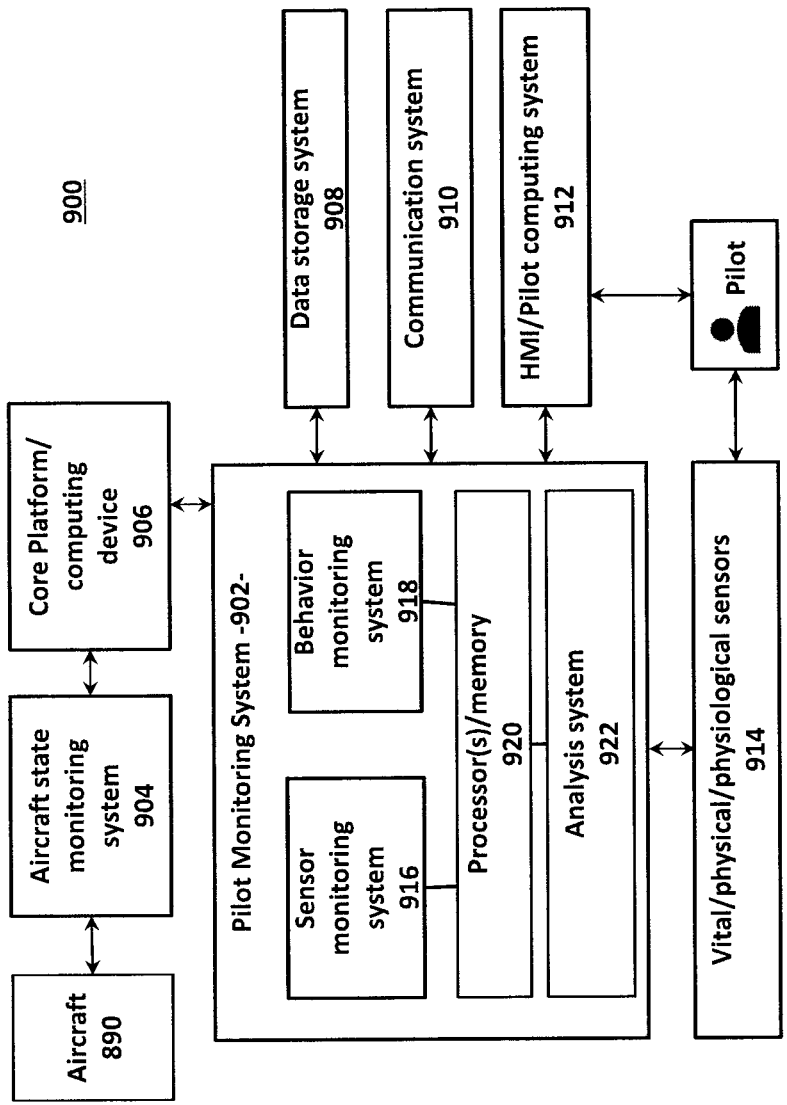
FIG. 9 illustrates a block diagram of an example pilot health monitoring system.
Figure 10:
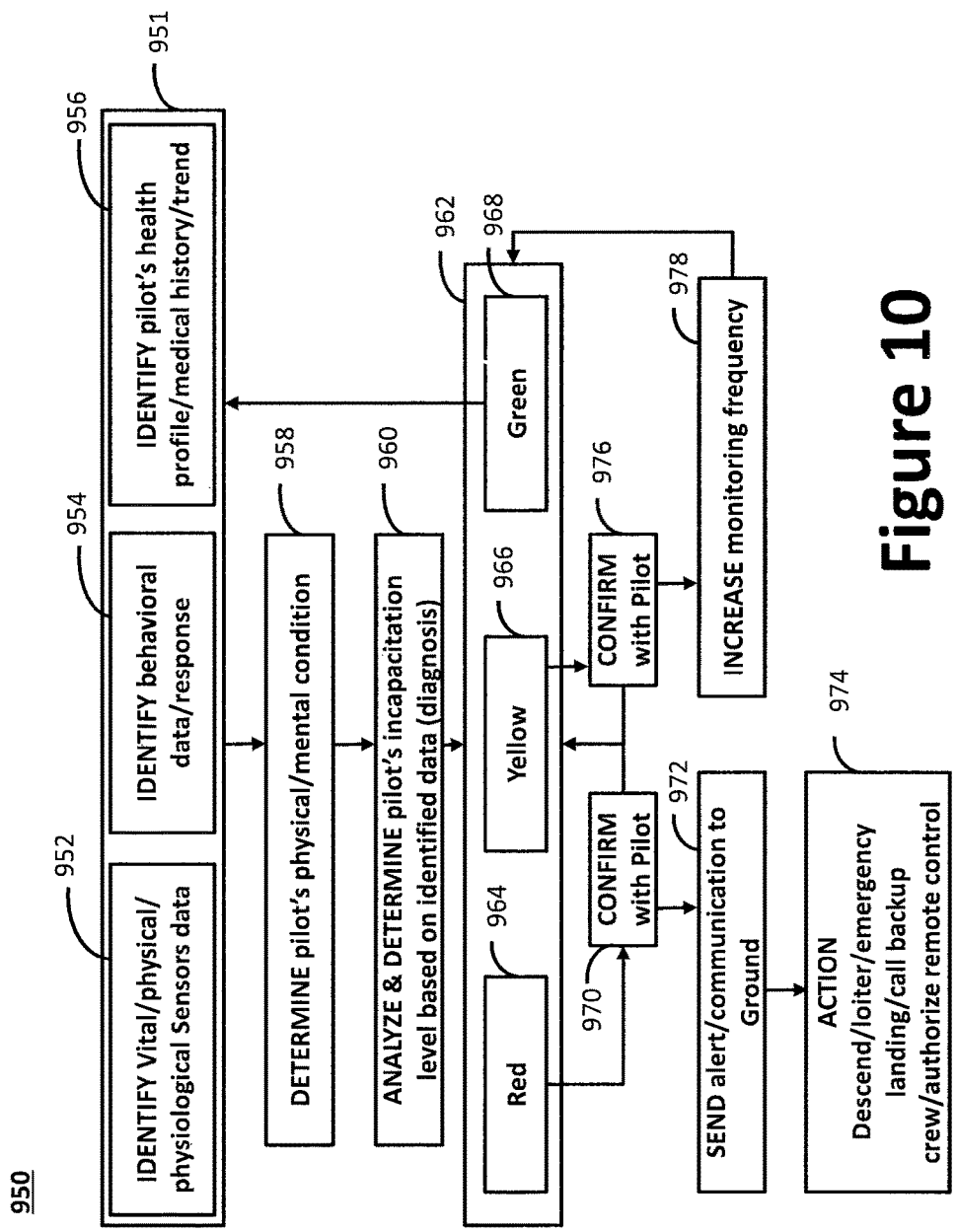
FIG. 10 illustrates an example pilot health monitoring procedure.

FIG. 8 illustrates an example emergency auto-land procedure 800. The example emergency auto-land procedure 800 demonstrates the ability of the aircrew automation system 100 to autonomously land the aircraft during three primary phases of auto-landing: approach, glideslope, and wheels on the ground.

The emergency auto-land procedure 800 builds upon the emergency descent procedure 700, which may be employed to lower the aircraft to a predetermined landing altitude (e.g., 4,000 feet at 210 knots) and on a course towards the glide slope of a runway. For example, the aircraft may circle in place at a predetermined landing altitude until an auto-land command is received at step 802. As noted above, a single command may be used to automatically begin the emergency descent procedure 700 and then the auto-land procedure 800 once the aircraft is positioned at a predetermined location, heading, and altitude. The auto-land command may, however, be triggered upon detection via the aircrew health monitoring system 160 of continued pilot incapacitation (i.e., the pilot has remains incapacitated), after which aircrew automation system 100 will operate the aircraft. In another example, the auto-land command may be triggered by a pilot voice command. For example, the co-pilot may recite a predetermined phrase (e.g., "Begin Landing Checklist") to signal to the aircrew automation system 100 that the pilot is still incapacitated.

At step 804, the aircrew automation system 100 adjusts the airspeed of the aircraft. For example, the aircrew automation system 100 may begin the landing procedure by reducing airspeed from 210 knots to 190 knots.

At step 806, the aircrew automation system 100 adjusts the control surfaces of the aircraft. For example, the aircrew automation system 100 adjust the flaps from UP to 1 degree.

At step 808, the aircrew automation system 100 again adjusts the airspeed of the aircraft. For example, the aircrew automation system 100 may reduce the airspeed to 150 knots.

At step 810, the aircrew automation system 100 again adjusts the control surfaces of the aircraft. For example, the aircrew automation system 100 adjust the flaps UP from 1 degree to 2 degrees, then to 10 degrees, and finally to 15 degrees.

At step 812, the aircrew automation system 100 adjusts the autobrake. For example, the aircrew automation system 100 may switch the autobrake from OFF to level 2.

At step 814, the aircrew automation system 100 waits until the glideslope is achieved. For example, the machine vision of the perception system 106 may observes that glideslope is achieved on the primary flight display (PFD), and commands the aircrew automation system 100 to continue the landing procedure at step 816.

At step 816, the aircrew automation system 100 actuates the landing gear (e.g., puts the landing gear down).

At step 818, the aircrew automation system 100 again adjusts the airspeed of the aircraft. For example, the aircrew automation system 100 may reduce the airspeed to 140 knots.

At step 820, the aircrew automation system 100 again adjusts the control surfaces of the aircraft. For example, the aircrew automation system 100 adjust the flaps UP from 15 degrees to 30 degrees.

At step 822, the aircrew automation system 100 moves to prepare for the final landing event (i.e., wheels on ground).

At step 824, the perception system 106 observes that landing is imminent and, after the throttles move to zero, the aircrew automation system 100 moves the throttles to the unlocked position to enable use of the reverse thrusters.

At step 826, the aircrew automation system 100 moves the reverse thrusters and the aircraft comes to rest on the runway.

In parallel with steps 804 through 826, the perception system 106 performs the landing checklist of step 828. For example, the perception system 106 may observe the actions of the aircrew automation system 100 during steps 804 through 826 (or shortly thereafter) to check items off a landing checklist (e.g., to ensure that the aircrew automation system 100 has performed the necessary actions). For example, the perception system 106 may verify each step before the auto-land procedure 800 may proceed to the next step. As explained with regard to the emergency descent procedure 700, the verification may be dynamic, or after a delay that can be expected in certain circumstances.

The auto-land procedure 800 may end at step 830 when the aircraft is taxiing from the runway or when the aircraft is parked (e.g., the engines are shut off).

The aircrew automation system 100 and derivative technologies may be applied across a wide range of aircraft and flight simulators. The derived flight performance characteristics from an aircraft flight test can be used to improve the fidelity of flight simulators used to train pilots. Providing flight simulators access to actual aircraft performance data has tremendous value for flight simulator operators. Another benefit of aircrew automation system 100 is its ability to synthesize flight performance characteristics when aircraft are modified for special flight plans such as the addition of sensors and antennas that can affect aerodynamic performance and flight handling qualities (e.g., aircraft development). In addition, the data captured by the aircrew automation system 100 can be used for aircraft health monitoring, using prognostics to sense maintenance needs.

The aircrew automation system 100 furthers the safety and utility of commercial aviation operations while providing significant savings in human operating costs. For example, the aircrew automation system 100 may be applied to long-haul air cargo carriers to increase safety and efficiency as well the cost-savings of this advanced pilot-assist technology. Further, the ultimate state machine, for example, may serve as a training tool for pilots in-flight, or as a safety system, providing a second set of eyes in what would traditionally be a single-pilot aircraft. Portions of the human-machine interface 126 streamline all piloted flight operations, even multi-crew operations.

In some examples described in FIGS. 8 through 13, systems and methods are disclosed to measure, analyze and determine the pilot's health condition based on multiple factors (e.g., pilot health statistics, vehicle state, historical data, etc.). For example, the disclosed method does not solely depend on the sensor readings. It also considers the pilot's individual tolerance level, pre-existing health condition, aircraft's state and operation, etc., in view of collected information from a variety of sensors. In addition, behavioral traits of the pilot are utilized as a secondary evidence to confirm or deny the sensor readings. An interaction between the pilot and the machine via a computerized user interface (i.e. tablet computers) is also utilized to fathom the pilot's ability to operate the aircraft during flight.

The disclosed systems and methods relate to measuring, analyzing, and classifying a health condition of a pilot based on measured health parameters. In some aspects, systems and methods determine whether and/or when an autonomous system, such as an autopilot, is to control an aircraft, and/or execute emergency landing procedures, based on the health condition. In particular, disclosed features assist the aircraft's autonomous system, via a core platform, to determine when to initiate the auto-landing procedure or other autonomous emergency protocols.

In one example, hypoxia, as well as hypoxemia, is a common condition developed while operating in a high-altitude environment. Hypoxia is caused by a lack of oxygen and/or partial pressure of oxygen in the breathing air, which is common at certain altitudes. Oxygen saturation levels in the operator's blood stream can decrease during extended periods of exposure to low-oxygen environments. For a pilot making frequent trips to a high-altitude environment, hypoxia can cause the pilot to become disoriented, fatigued, incapacitated, etc., during aircraft operation. While aircraft are often equipped to be pressurized during flight, symptoms of hypoxia and other acute medical conditions can still effect some pilots, jeopardizing not only the safety of the pilot, but also the passengers on board.

Core Platform 906/Computing Device.

Core platform 906 is a centralized processing unit configured to analyze and/or control all system functions. The core platform 906 may provide, or otherwise serve as, middleware that can be made specific to a particular aircraft or configuration through an initial transition and setup phase, in a manner similar to core platform 102 described with respect to FIGS. 1 and 2. In other words, core platform 906 may include a mission control system (e.g., similar to mission control system 110) and/or may provide an operating system (e.g., similar to operating system 206) that provides services to a set of operational applications (e.g., similar to operational applications 202) and output signals to one or more of a set of hardware interfaces or HMI system 912, while collecting and logging the data necessary to enable those applications.

The core platform 906 serves as the primary autonomous agent and decision-maker, which synthesizes inputs from the aircraft state monitoring system 904, the pilot monitoring system 902, data storage system 908, communication system 910, sensors 914, and HMI system 912, with its acquired knowledge base to determine the overall system state. The core platform 906 may employ a processor to process inputs from the various sensor suites or subsystems and aggregate the resultant information into an understanding of current aircraft state, pilot health, etc. The resultant information may be compared against one or more aircraft and/or pilot specific files that inform the core platform's understanding of pilot actions, pilot health, system state, and understanding of appropriate procedures as they relate to the pilot monitoring system 902. The resultant information and associated determinations can be passed to a human pilot via the HMI system 912 or, in certain aspects, to a flight control system (e.g., similar to flight control system 116) and/or an actuation system (e.g., similar to actuation system 108) to enable autonomous operation. In some examples, an emergency landing procedures and corresponding system may be in communication with the core platform. Multiple other systems may be centrally managed by a single core, or managed remotely via one or more networks.

Aircraft State Monitoring 904.

The aircraft state monitoring system communicates with an aircraft control system and/or a plurality of sensors to identify the aircraft's mechanical and/or operational condition. As described herein, a mechanical condition (e.g., functional status of an air pressurization system) and/or an operational condition (e.g., altitude, airspeed, etc.) of the aircraft can have an impact on the pilot's health condition. For example, the pilot monitoring system 902 is in communication with the aircraft state monitoring system 904, such as via the core platform. When a situation develops within the aircraft that threatens the pilot's health condition (e.g., a failure of the air pressurization system, the cabin temperature cannot be sustained, failure of other "life support" systems, etc.), the pilot monitoring system 902 may increase the frequency in taking health parameter measurements from the pilot. Based on a determination of a state of the aircraft, and/or a determination of the pilot's health condition, the core platform 906 may identify a correlation between the determined aircraft state and the pilot's collected health information (e.g., health parameters, vital signs, etc.). Such protocols, definitions, and/or relationships may be pre-defined and stored in a data storage system 108.

In an example, a sudden unexpected increase in a rate of climb of the aircraft is expected to increase the pilot's heart rate. The system identifies that the cause of the change in the measured pilot health condition (e.g., heart rate increase) is in response to the aircraft's operational state, not in response to a health emergency (e.g., a heart attack). Similarly, phases of flight may be monitored by the aircraft state monitoring system weigh specific information differently during critical phases of flight. For instance, during take-off and landing, the pilot may experience increase blood pressure, heart rate, respiratory rate, etc., as a normal response to the increase of adrenaline associated with the flight activity. Such flight path and phase correlations may be identified ahead of time, such that the system anticipates when and/or where to apply a different standard in information analysis for determining the pilot's health status. Additionally or alternatively, a determination on when and/or how to respond, such as a frequency and/or a type of response (e.g., warning, aircraft control), can be based on the determined aircraft state and pilot health condition in view of a particular correlation and/or weighted standard.

Pilot Monitoring System 902.

The pilot monitoring system 902 includes subsystems to aid in execution of the pilot monitoring function. A sensor monitoring system 916 is configured to analyze data from one or more sensors 914 (e.g., a vital signs sensor, a physical sensor, a physiological sensor, a camera, etc.) and other sources (e.g., data storage system 908, HMI 912, aircraft state monitoring system 904) to determine a health condition of the pilot. Sensors 914 may include, but are not limited to, a sensor circuit detecting an electrocardiogram (ECG) signal(s), a sensor circuit detecting a respiration rate signal indicative of the breathing of the patient and a sensor circuit detecting the movement and/or posture of the patient, such as an accelerometer, 3-axis accelerometer, altimeter, gyroscope, and the like, smell/odor sensors, video/picture sensors, speech/sound sensors, and the like.

A behavioral monitoring system 918 is configured to use data from the sensors 914 and other sources (e.g., HMI 912, system 904) to determine a behavioral characteristic that indicates the pilot's fitness to operate the aircraft 890. The pilot monitoring system 902 includes a processor/memory 920, which is configured to store and execute machine-readable instructions to aid in information collection and analysis, via, for example, analysis system 922.

Sensor Monitoring System 916.

There are multiple avenues to determine a pilot's fitness to operate an aircraft 890. Physiological parameters of the pilot may be measured using various sensors 914. These measurements can often indicate a symptom of a certain medical/health condition. When more than one sensors 914 are combined, the accuracy of any diagnosis increases. For instance, many medical conditions are associated with multiple symptoms, with some symptoms being common to a variety of medical conditions. A sensor monitoring system 916 identifies the measurable state of the pilot using these sensors 914.

In some situations, a pilot's collected information (e.g., vital signs) appear normal, yet the pilot may be unfit to operate a vehicle. For example, the pilot may be mentally disoriented or mentally incapacitated, even as the information from the sensors 914 indicate that the pilot is physically able to operate the vehicle. In this case, the pilot's physiological measurements can register in an acceptable range.

Behavior Monitor System 918.

An additional or alternative source of information can come from an analysis of the pilot's behavior, such as movements, facial expression, reaction time, etc. A behavioral analysis of the pilot is performed by the behavior monitor system 918 from information collected via the sensors 914.

Behavior analysis can be used to identify symptoms of mental inability to operate the vehicle. (e.g., movement pattern, response time, type of response, etc.). As such, in some examples, the pilot's fitness to operate the vehicle may be determined, at least in part, based on observing his/her behavior. Thus, behavioral analysis can be combined with other data (e.g., vital signs, aircraft state information, etc.) to increase accuracy of the pilot's determined state.

Traits associated with analysis and/or determination of a pilot's behavior can includes gait analysis, eye movement, eye dilation, physical movement pattern, speech pattern, and the like. Behavioral traits of the pilot can also help identify a pilot's level of fatigue. For example, measurements associated with traits corresponding to the pilot's normal behavior may be stored in the data storage 908 (and/or processor/memory 920) as an expected behavior, to which measured pilot behaviors can be compared. Based on such comparison, a state of the pilot's health may be partially determined based on measurements of one or more health parameters. In addition, behavioral symptoms may be identified based on a measured interaction between the pilot and a computerized user interface, such as a human-machine interface (HMI) 912 (e.g., a tablet-computing device, integrated vehicle control panel, etc.).

In an example, the system 900 may present to the pilot a series of questions via the HMI 912. The accuracy of the response and the response time may be an indicator of certain cognitive impairments. In some examples, the system 900 may request the pilot to perform one or a series of physical actions, such as enter a code, trace a pattern, answer a series of questions, etc. The accuracy and timing of the pilot's response may indicate a physical or cognitive impairment that may affect the pilot's fitness to operate the aircraft. The system 900 also may record and monitor the pilot's interaction with the HMI 912 to identify a trend or specific input that corresponds to an abnormality. Standards and/or thresholds of abnormality, accuracy, response time, and the like may be stored by the data storage 908 as model references for future comparison.

Analysis System 922.

Once parameter data is gathered from the sensor monitoring system 916 and behavior monitoring system 918, the monitoring system 902 analyzes the information to make a determination as to the pilot's health condition. As discussed above, protocols, relations, standards may be predefined. The analysis system 922 may apply different weight to each of the factors used to determine the pilot's health condition and/or overall fitness to operate the aircraft 890. For example, a blood oxygen measurement may be assigned a higher weigh than a pupil dilation measurement in determining a diagnosis of hypoxia. These weights may be predetermined and stored by the storage device. Scenarios may be pre-determined as well, such as during landing and take-off procedures, as described, supra.

The analysis system 922 may also reference an individual pilot's medical history (e.g., pre-existing medical conditions), trends, and the like. Pilot specific information can be stored and on and accessed from the data storage system 108, the processor/memory 920, or both. Each individual has a different tolerance to external conditions. In other words, different individuals in the same environment will react differently. For example, a person residing in a higher-altitude location would more easily tolerate a decline in blood oxygen saturation level (e.g., due to hypoxia, hypoxemia) than those residing in a lower-altitude location. This is because of the time it takes for an individual to acclimatize to a higher altitude.

In one example, both categories of indications, behavioral and vital, may be combined to determine an incapacitation level and/or alert level corresponding to the pilot's health condition. Depending on the determined incapacitation level and/or alert level, the core platform 906 may direct different actions be taken. For example, if the analysis system 922 determines the situation requires immediate action (e.g., in response to the aircraft state and/or the pilot's physical condition), the aircraft may enter an autopilot mode to prevent a catastrophic end (e.g., initiate a landing procedure or descend-and-loiter procedure). The table below shows an exemplary alert definition. It is apparent that those having ordinary skill in the art would understand the possible variant protocols to define the alert level.

Data Storage System 108.

Data storage system 108 contains schema to define relationships between symptoms, historical data, trends, and/or diagnosis of the pilot's condition. Instructions and/or data to define the relationship are stored in storage system 108, such as weights, definitions, and/or protocols for various situations and/or individuals. The data can draw correlations between symptoms and conditions, and aid in analysis of particular situations. Data written to the storage system 108 may be modified as the system 900 identifies patterns during particular operations, from a particular individual pilot, a particular aircraft/vehicle, etc.

FIG. 2 illustrates a method for determining the pilot's health condition in an exemplary flowchart. As shown in step 951, sensor and/or stored data is collected, such as physiological sensor data in step 952, behavioral data in step 954, and the medical profile of the pilot in step 956. The state of the pilot's health condition can be determined in step 958. The system analyzes the data in step 960 to decide to which categories found in step 963 the determined condition belong. For example, red in step 964 indicates high severity, yellow in step 966 indicates low severity, and green in step 968 indicates normal. As shown in FIG. 11, the combination of categories (red, yellow, green) determined for each type of sensor data (e.g., physiological and/or behavioral), ultimately determines the overall condition (e.g., incapacitation and/or alert level) of the pilot's fitness.

If the pilot's fitness is determined to be other than normal (e.g., red 964, yellow 966) the pilot may be prompted by the system 900 (e.g., via HMI and/or other GUI) to confirm the machine-determined state of the pilot's condition, in steps 970 and 976. Confirmation serves as a fail-safe step, such as before the automated system is commanded to take action in step 974, if the pilot's incapacitation diagnosis is erroneous. Similarly, a question may be asked to the ground station via the communication system. Such fail-safe safety protocol would be different per organizations and aircraft's objectives. In some embodiments, the communication among the one or more computer or the one or more processors alike, may support a plurality of encryption/decryption methods and mechanisms of various types of data.

In some embodiments, an alert may be sent via the communication system to ground station, in step 972. Additionally or alternatively, actions can be taken if the pilot fails to confirm the request in step 970. As shown in step 974, the ground crew may take over to remote control the aircraft. Additionally or alternatively, the ground crew may also prepare for auto-landing procedure at the airport. The aircraft may enter a descend and loiter procedure to lower the altitude which may help the pilot to return to normal state. In some embodiments, an alert may be sent to another crew on board to take over the operation of the vehicle. The "take action" may include the system to provide an instruction to the pilot to remedy the symptoms. For example, the system may identify a medical procedures/types of medication the pilot should take. The system also may suggest the pilot to stretch before declaring any alert status.

In some examples, even if the pilot is able to respond to a confirmation request in step 976, due to the initial red or yellow classification, the system can return to step 962 increase monitoring frequency. This provides the system 900 with a greater data set with which to determine the pilot's continued fitness to operate the aircraft 90.

Vital/Physical/Physiological Sensors 914.

Figure 12:
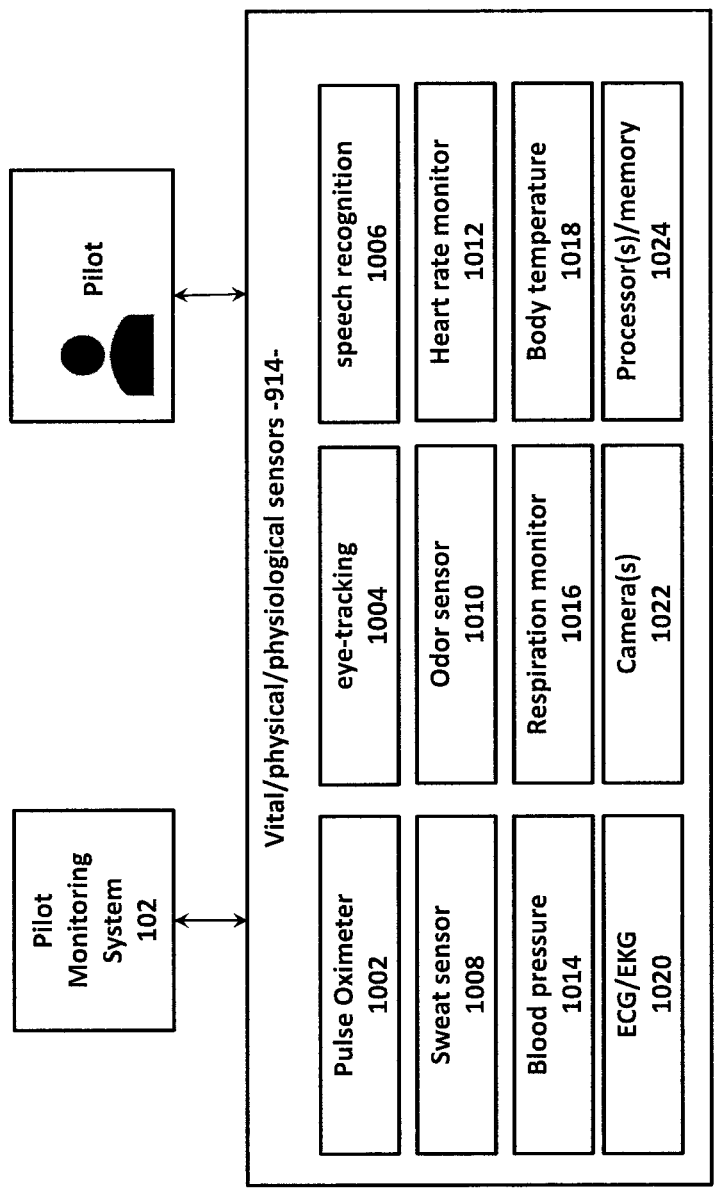
FIG. 12 illustrates an example pilot monitoring system.

FIG. 12 illustrates a non-limiting list of sensors to capture information of parameters regarding the pilot's health condition. One or more of the various sensors 914 can be included or excluded, including any combination thereof, and addition of other sensors known or developed later. In some examples, the sensors 914 may be integrated with and/or implemented as a wearable device including, but not limited to, a fashion accessory (e.g., a wrist band, a ring, etc.), a utility device (e.g., a handheld baton, a pen, an umbrella, a watch, etc.), an article of clothing, or any combination thereof.

In some examples, the components of system may be integrated with or implemented as a wearable device including, but not limited to, a fashion accessory (e.g., a wrist band, a ring, etc.), a utility device (a handheld baton, a pen, an umbrella, a watch, etc.), a body clothing, or any combination thereof.

The types of sensors 914 contemplated herein monitor patient's vitals, among other features, which may include, but are not limited to, heart rate, blood pressure(s), body weight, concentration of one or more metabolite(s) in the blood, concentration of one or more gas(es) in the blood, temperature, asystole, respiration, electrocardiogram, vital signs, activity from accelerometer(s), activity from gyroscope(s), ECG beat detection and classification, ECG rhythm classification, electrocardiogram (ECG) interpretation, ECG-ST segment analysis, ECG-QT measurement, cardiac output, heart rate variability, temperature(s), blood gas (including oxygen)

A pulse oximeter 1002 measures blood oxygen saturation level. For example, a 93% level is considered the lower limit for normal or tolerated oxygen saturation. Oxygen saturation levels at each altitude is different, however. For instance, achieving an altitude of 12,000 feet, a pilot may have an oxygen saturation of approximate 85%. However, the system will understand this is a normal reading based on the altitude and correlations stored in data storage system 108.

As noted, each individual may react differently, which may cause incapacitation or fatigue in a particular pilot. Thus, a required level of O2 for a pilot to function normally can depend on individual pilot's tolerance level, which can be determined from historical data stored in data storage system 108. A pilot is recommended to maintain their oxygen saturation level at a minimum of 90%. A low (even relatively low) oxygen saturation level can lead to altitude-induced hypoxia. This lack of oxygen (hypoxia) can affect a pilot's cognitive ability, which can lead to the pilot's inability to comprehend critical tasks, such as a clearance, how to calculate fuel consumption, and/or respond to an emergency situation.

Eye-tracking sensors 1004, such as implemented in glasses and/or a helmet, can measure pupil movement and/or dilation. For example, pupil/eye dilation can indicate hypoxia, which can cause a drop in the pilot's vision. Under low light conditions, visual degradation has been demonstrated at altitudes between 4,000 and 5,000 feet. In addition, under daylight conditions, visual degradation has been shown to occur at 10,000 feet. Eye-tracking systems 1004 can also aid in measuring fatigue and/or alertness levels.

Speech and pattern recognition sensor 1006 can measure and recognize if a pilot is slurring his/her speech, which can be an indication of fatigue, dysarthria (neurological condition, such as stroke), etc. A historical record corresponding to the pilot's normal speech pattern can be stored in data storage system 108 as a model for reference.

In some examples, a sweat sensor 1008, such as a wearable patch, can be worn by the pilot to analyze chemicals in the pilot's sweat. Such chemical analysis can be indicative of stress on the pilot, and/or if something has gotten into the pilot's system (e.g., virus, food poisoning, etc.). Similarly, an odor sensor 1010 can serve as an electric nose to analyze chemicals, odors, within the environment and/or of the pilot.

Several sensors can be used to measure specific pilot vital signs, such as heart rate monitor 1012, blood pressure sensor 1014, respiration sensor 1016 (to monitor breathing rate of hyperventilation), body temperature sensor 1018, to monitor for hyperthermia and hypothermia, ECG/EKG 1020 to monitor cardiopulmonary conditions.

One or more cameras 1022 can be employed to monitor for health conditions as well as operator behaviors, including facial movement, gait pattern, skin tone, complexion, etc. For example, facial movements can be indicators of fatigue; skin tone and/or complexion changes can represent certain medical conditions, such as hyperthermia; and an unusual gait pattern can indicate a level of fatigue or stress.

Moreover, a processor and/or memory 1024 can be included, to aid in information capture and/or analysis of data. Further, signals from the various sensors may require formatting to be readable by different systems, such as the core platform.

Figure 13:
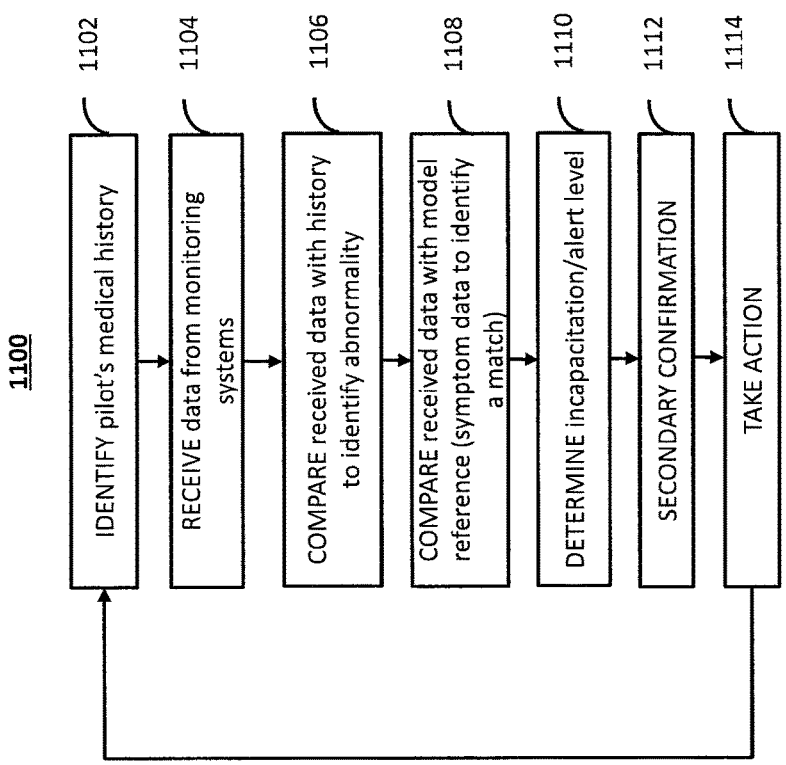
FIG. 13 illustrates another example pilot health monitoring procedure.

FIG. 13 describes another example method of the system 900. In step 1102, the pilot's medical history is accessed. In step 1104, data from the monitoring system (e.g., aircraft state information, sensor input, etc.) is received at the system 900 (e.g., at the core platform). In step 1106, the system compares the obtained monitored data to a medical history of the pilot to identify any abnormality that is not in line with the trends shown in the history. The definition of abnormality would depend on the individual's normal physical response/trend/history. In step 1108, data is compared to model references to identify a match of symptoms to one or more health conditions. Output from one or both of the comparisons may be employed to demine incapacitation and/or alert level in step 1110, depending on the type of data being measured, stock of stored values, phase of vehicle operation, etc. For example, response time/movement pattern may be subjective to the historical and/or trend data. However, a pulse oximeter measurement may be objectively compared to the model references (a set value or range). Further, depending on the particular stage of flight, environmental conditions, individual medical record, etc., some data may be weighed more heavily than other data. In step 1112, the pilot may be presented with a warning and/or request for a response to confirm the diagnosis. In step 1114, actions may be taken to address the determined condition. Additionally or alternatively, the method can return to step 1102 and continue monitoring the pilot's condition.

Possible modifications to implementation of the pilot monitoring system 902 include adjusting emergency procedures and/or symptoms database information. Additionally or alternatively, the alert level can be predetermined, yet adjusted in view of historical data, trend analysis, and/or calibration to a specific vehicle and/or individual pilot.

Moreover, the sensors can be positioned and/or located at various places within the cabin and/or on the pilot depending on the specification of each sensor, the particular operating task, and/or desired information. In some examples, adaptations to communication protocols can be made, to accommodate different systems and/or availability to networks, remote updates, etc.

The above-cited patents and patent publications are hereby incorporated by reference in their entirety. Although various embodiments have been described with reference to a particular arrangement of parts, features, and like, these are not intended to exhaust all possible arrangements or features, and indeed many other embodiments, modifications, and variations may be ascertainable to those of skill in the art. Thus, it is to be understood that the invention may therefore be practiced otherwise than as specifically described above.

What is claimed is:

1. A pilot monitoring system for use in an aircraft, the pilot monitoring system comprising:
    a plurality of sensors configured to monitor one or more health parameters of a pilot;
    an aircraft state monitoring system configured to determine flight situation data of the aircraft;
    an analysis system to determine, via one or more processors, an incapacitation level of the pilot as a function of the one or more health parameters;
    a human machine interface operatively coupled with the one or more processors to provide an interface between the pilot and the pilot monitoring system, the human machine interface configured to present a warning to the pilot as a function of the determined incapacitation level; and
    an actuation system operatively coupled with the one or more processors to adjust or actuate one or more flight controls of the aircraft as a function of the determined incapacitation level, wherein the actuation system is configured to perform an emergency descent procedure and an auto-landing procedure,
    wherein, during the emergency descent procedure, the pilot monitoring system is configured to navigate the aircraft, via the actuation system, to a predetermined airspeed and a predetermined altitude, and
    wherein, during the auto-landing procedure, the pilot monitoring system is configured to navigate the aircraft, via the actuation system, from the predetermined altitude to a touchdown location.

2. The pilot monitoring system of claim 1, wherein the pilot monitoring system is configured to monitor one or more health parameters for each of a plurality of pilots, wherein the human machine interface is configured to display the one or more health parameters for each of the plurality of pilots.

3. The pilot monitoring system of claim 1, wherein the one or more health parameters includes both a physiological state and a behavioral state of the pilot.

4. The pilot monitoring system of claim 1, wherein, during the emergency descent procedure, the actuation system is configured to automatically: (1) adjust or actuate the one or more flight controls to descend the aircraft from a cruising altitude to the predetermined altitude; (2) adjust or actuate the one or more flight controls to slow the aircraft from a cruising airspeed to the predetermined airspeed; (3) alert an air traffic control facility of an emergency situation; and (4) set and hold the aircraft in a holding pattern at or near its current position.

5. The pilot monitoring system of claim 1, wherein, during the auto-landing procedure, the actuation system is configured to automatically: (1) adjust or actuate the one or more flight controls; (2) adjust an airspeed of the aircraft; (3) adjust or actuate an autobrake; (4) determine a glideslope for the aircraft to the touchdown location; (5) adjust or actuate landing gear; and (6) adjust or actuate one or more reverse thrusters.

6. The pilot monitoring system of claim 1, wherein the actuation system is configured to control secondary flight controls of the aircraft during the auto-landing procedure.

7. The pilot monitoring system of claim 6, wherein the actuation system includes an XY-plotter defining a Y-axis and an X-axis, a tool to engage at least one of the secondary flight controls of the aircraft, and a control system to move the tool along the Y-axis and the X-axis.

8. The pilot monitoring system of claim 1, wherein the plurality of sensors includes one or more optical sensors to monitor the pilot visually, wherein the pilot monitoring system determines a behavioral state of the pilot as a function of information gathered by the one or more optical sensors.

9. The pilot monitoring system of claim 8, wherein the pilot monitoring system is configured to determine whether the pilot is incapacitated based at least in part on the behavioral state for the pilot.

10. The pilot monitoring system of claim 8, wherein the analysis system is configured to compute a point of gaze for the pilot using one or more eye-tracking techniques, wherein the pilot monitoring system is configured to determine whether the pilot is incapacitated based at least in part on the point of gaze for the pilot.

11. The pilot monitoring system of claim 1, wherein the pilot monitoring system is configured to gather the one or more health parameters for the pilot using one or more wearable vital sensors associated with the pilot.

12. The pilot monitoring system of claim 1, wherein the human machine interface is configured to display a plurality of tasks via a touch screen display in a form of a task list during the auto-landing procedure, wherein each of the plurality of tasks is marked as either completed or not completed during the auto-landing procedure based at least in part on an input provided via the touch screen display or an operation of the aircrew automation system.

13. The pilot monitoring system of claim 1, wherein the plurality of sensors is configured to monitor one or more cockpit instruments of the aircraft visually to generate the flight situation data.

14. A method for monitoring a pilot in an aircraft using an automation system, the method comprising the steps of:
monitoring, via a plurality of sensors, one or more health parameters for the pilot;
determining, via an aircraft state monitoring system, flight situation data of the aircraft;
determine, via an analysis system, an incapacitation level of the pilot, wherein incapacitation level is determined as a function of the one or more health parameters;
presenting a warning to the pilot, via a human machine interface, as a function of the determined incapacitation level, wherein the human machine interface is configured to provide an interface between the pilot and the automation system;
adjusting or actuating, via an actuation system, one or more flight controls of the aircraft as a function of the determined incapacitation level;
performing an emergency descent procedure as a function of the determined incapacitation level, wherein, during the emergency descent procedure, the automation system is configured to navigate the aircraft, via the actuation system, to a predetermined airspeed and a predetermined altitude; and
performing an auto-landing procedure, wherein, during the auto-landing procedure, the automation system is configured to navigate the aircraft, via the actuation system, from the predetermined altitude to a touchdown location.

15. The method of claim 14, wherein, during the auto-landing procedure, the actuation system is configured to automatically: (1) adjust or actuate the one or more flight controls; (2) adjust an airspeed of the aircraft; (3) adjust or actuate an autobrake; (4) determine a glideslope for the aircraft to the touchdown location; (5) adjust or actuate landing gear; and (6) adjust or actuate one or more reverse thrusters.

16. The method of claim 14, wherein the automation system is configured to gather the one or more health parameters for the pilot using one or more wearable vital sensors associated with the pilot.

17. The method of claim 14, wherein the plurality of sensors includes one or more optical sensors to monitor the pilot visually, wherein the automation system is configured to determine a behavioral state of the pilot as a function of information gathered by the one or more optical sensors.

18. The method of claim 14, further comprising the step of computing a point of gaze for the pilot through one or more eye-tracking techniques, wherein the pilot monitoring system is configured to determine whether the pilot is incapacitated based at least in part on the point of gaze for the pilot.

19. The method of claim 14, wherein the plurality of sensors is configured to monitor one or more cockpit instruments of the aircraft visually to generate the flight situation data.

20. A pilot monitoring system for use in an aircraft, the pilot monitoring system comprising:
a plurality of sensors configured to monitor one or more health parameters of a pilot;
an aircraft state monitoring system configured to determine flight situation data of the aircraft;
an analysis system to determine, via one or more processors, an incapacitation level of the pilot as a function of the one or more health parameters;
a human machine interface operatively coupled with the one or more processors to provide an interface between the pilot and the pilot monitoring system, the human machine interface configured to present a warning to the pilot as a function of the determined incapacitation level; and
an actuation system operatively coupled with the one or more processors to adjust or actuate one or more flight controls of the aircraft as a function of the determined incapacitation level,
wherein the actuation system is configured to perform an auto-landing procedure, and
wherein, during the auto-landing procedure, the pilot monitoring system is configured to navigate the aircraft, via the actuation system, to a touchdown location.

21. The pilot monitoring system of claim 20, wherein the actuation system is configured to perform an emergency descent procedure as a function of the determined incapacitation level, wherein, during the emergency descent procedure, the pilot monitoring system is configured to navigate the aircraft, via the actuation system, to a predetermined airspeed and a predetermined altitude.

22. The pilot monitoring system of claim 20, wherein, during the emergency descent procedure, the actuation system is configured to automatically: (1) adjust or actuate the one or more flight controls to descend the aircraft from a cruising altitude to the predetermined altitude; (2) adjust or actuate the one or more flight controls to slow the aircraft from a cruising airspeed to the predetermined airspeed; (3) alert an air traffic control facility of an emergency situation; and (4) set and hold the aircraft in a holding pattern at or near its current position.

23. The pilot monitoring system of claim 20, wherein, during the auto-landing procedure, the actuation system is configured to automatically: (1) adjust or actuate the one or more flight controls; (2) adjust an airspeed of the aircraft; (3) adjust or actuate an autobrake; (4) determine a glideslope for the aircraft to the touchdown location; (5) adjust or actuate landing gear; and (6) adjust or actuate one or more reverse thrusters.

24. The pilot monitoring system of claim 20, wherein the plurality of sensors includes one or more optical sensors to monitor the pilot visually, wherein the pilot monitoring system determines a behavioral state of the pilot based at least in part on the visual monitoring gathered by the one or more optical sensors.

25. The pilot monitoring system of claim 20, wherein the pilot monitoring system is configured to monitor one or more health parameters for each of a plurality of pilots, wherein the human machine interface is configured to display the one or more health parameters for each of the plurality of pilots.

* * * * *